(12) United States Patent
Slager et al.

(10) Patent No.: US 8,936,811 B2
(45) Date of Patent: Jan. 20, 2015

(54) DEVICE COATED WITH GLYCOGEN PARTICLES COMPRISING NUCLEIC ACID COMPLEXES

(75) Inventors: Joram Slager, St. Louis Park, MN (US); Joseph Schmidt McGonigle, Minneapolis, MN (US)

(73) Assignee: SurModics, Inc., Eden Prairie, MN (US)

( * ) Notice: Subject to any disclaimer, the term of this patent is extended or adjusted under 35 U.S.C. 154(b) by 751 days.

(21) Appl. No.: 12/437,287

(22) Filed: May 7, 2009

(65) Prior Publication Data

US 2009/0280181 A1 Nov. 12, 2009

Related U.S. Application Data

(60) Provisional application No. 61/051,041, filed on May 7, 2008.

(51) Int. Cl.
*A61K 9/14* (2006.01)
*A61K 31/7052* (2006.01)
*A61P 43/00* (2006.01)

(52) U.S. Cl.
USPC ........... 424/484; 424/489; 424/499; 514/44 R

(58) Field of Classification Search
CPC . A16K 9/0024; A16K 9/1641; A16K 9/1652; A16K 9/1623; A16K 9/1658; A16K 47/48046; A16K 47/48176; A16K 47/48192; A16K 47/482; A16K 47/48215; A16K 47/4823; A16K 47/48853; A16K 47/48861; A16K 47/48992; A16K 48/00; C12N 15/87
See application file for complete search history.

(56) References Cited

U.S. PATENT DOCUMENTS

| | | |
|---|---|---|
| 2,668,156 A | 2/1954 | Caldwell et al. |
| 4,060,506 A | 11/1977 | Verbanac |
| 4,079,025 A | 3/1978 | Young et al. |
| 4,638,045 A | 1/1987 | Kohn et al. |
| 5,116,927 A | 5/1992 | Floyd et al. |
| 5,160,745 A | 11/1992 | Deluca et al. |
| 5,272,181 A | 12/1993 | Boehmer et al. |
| 5,407,609 A | 4/1995 | Tice et al. |
| 5,414,075 A | 5/1995 | Swan et al. |
| 5,466,233 A | 11/1995 | Weiner et al. |
| 5,488,102 A | 1/1996 | Vetter |
| 5,514,379 A | 5/1996 | Weissleder et al. |
| 5,563,056 A | 10/1996 | Swan et al. |
| 5,589,577 A | 12/1996 | Peltonen et al. |
| 5,626,863 A | 5/1997 | Hubbell et al. |
| 5,668,193 A | 9/1997 | Gouda et al. |
| 5,705,270 A | 1/1998 | Soon-Shiong |
| 5,714,360 A | 2/1998 | Swan et al. |
| 5,733,994 A | 3/1998 | Koepff et al. |
| 5,736,371 A | 4/1998 | Samain et al. |
| 5,770,229 A | 6/1998 | Tanihara et al. |
| 5,773,021 A | 6/1998 | Gurtler et al. |
| 5,837,747 A | 11/1998 | Soon-Shiong et al. |
| 5,866,165 A | 2/1999 | Liu et al. |
| 5,866,619 A | 2/1999 | Sintov et al. |
| 5,879,707 A | 3/1999 | Cartilier et al. |
| 5,885,615 A | 3/1999 | Chouinard et al. |
| 5,980,948 A | 11/1999 | Goedemoed et al. |
| 5,993,530 A | 11/1999 | Tanaka et al. |
| 6,001,395 A | 12/1999 | Coombes et al. |
| 6,007,833 A | 12/1999 | Chudzik et al. |
| 6,073,040 A | 6/2000 | Kiyuna |
| 6,077,698 A | 6/2000 | Swan et al. |
| 6,156,345 A | 12/2000 | Chudzik et al. |

(Continued)

FOREIGN PATENT DOCUMENTS

| | | |
|---|---|---|
| EP | 0405917 | 1/1991 |
| EP | 1060741 | 9/2003 |

(Continued)

OTHER PUBLICATIONS

Hatefi, et al. (Apr. 2007) "Adenoviral Gene Delivery to Solid Tumors by Recombinant Silk-Elastinlinke Protein Polymers", Pharmaceutical Research, 24(4): 773-79.*
Howard, Kenneth A. et al., "Formulation of a microparticle carrier for oral polyplex-based DNA vaccines," *Biochimica et Biophysica Acta 1674*, 2004, 149-157.
Saul, Justin M. et al., "Delivery of non-viral gene carriers from sphere-templated fibrin scaffolds for sustained transgene expression," *Biomaterials* (2007); doi: 10.1016/j.biomaterials.2007.07.026. Jul. 26, 2007, 1-12.
Sethuraman, Vijay A. et al., "pH-Responsive Sulfonamide/PEI System for Tumor Specific Gene Delivery: An in Vitro Study", *Biomacromolecules* (7) 2006, 64-70.

(Continued)

*Primary Examiner* — Robert M Kelly
(74) *Attorney, Agent, or Firm* — Pauly, DeVries Smith & Deffner, LLC.

(57) ABSTRACT

Embodiments of the invention include particles with nucleic acid complexes, medical devices including the same and related methods. In an embodiment, the invention can include a method of making a medical device. The method can include contacting nucleic acids with cationic carrier agents to form nucleic acid complexes, adsorbing the nucleic acid complexes to porous particles to form nucleic acid complex containing particles, mixing the nucleic acid complex containing particles with a polymer solution to form a coating mixture, and applying the coating mixture to a substrate. In an embodiment, the method can include contacting nucleic acids with cationic carrier agents to form nucleic acid complexes, combining the nucleic acid complexes with a material to form nucleic acid complex containing particles in situ, mixing the nucleic acid complex particles with a polymer solution to form a coating mixture, and applying the coating mixture to a substrate. In an embodiment, the invention can include an implantable medical device including a substrate, an elution control matrix disposed on the substrate; a plurality of particles disposed within the elution control matrix, and a plurality of nucleic acid complexes disposed within the particles, the nucleic acid complexes comprising a nucleic acid and a cationic carrier agent. Other embodiments are included herein.

5 Claims, 14 Drawing Sheets

(56) References Cited

U.S. PATENT DOCUMENTS

| | | | |
|---|---|---|---|
| 6,197,757 B1 | 3/2001 | Perrier et al. | |
| 6,277,899 B1 | 8/2001 | Bastioli et al. | |
| 6,303,148 B1 | 10/2001 | Hennink et al. | |
| 6,346,263 B1 | 2/2002 | Mercier et al. | |
| 6,388,047 B1 | 5/2002 | Won et al. | |
| 6,410,044 B1 | 6/2002 | Chudzik et al. | |
| 6,410,517 B1 | 6/2002 | Truong et al. | |
| 6,419,957 B1 | 7/2002 | Lenaerts et al. | |
| 6,514,734 B1 | 2/2003 | Clapper et al. | |
| 6,583,219 B2 | 6/2003 | Won et al. | |
| 6,586,493 B1 | 7/2003 | Massia et al. | |
| 6,596,699 B2 | 7/2003 | Zamora et al. | |
| 6,596,860 B1 | 7/2003 | Kesselmans et al. | |
| 6,613,563 B1 * | 9/2003 | Sosnowski et al. | 435/320.1 |
| 6,660,827 B2 | 12/2003 | Loomis et al. | |
| 6,703,048 B1 | 3/2004 | Bengs et al. | |
| 6,706,288 B2 | 3/2004 | Gustavsson et al. | |
| 6,709,668 B2 | 3/2004 | Won et al. | |
| 6,716,445 B2 | 4/2004 | Won et al. | |
| 6,719,750 B2 | 4/2004 | Varner et al. | |
| 6,748,954 B2 | 6/2004 | Lee et al. | |
| 6,770,740 B1 | 8/2004 | Rice et al. | |
| 6,846,809 B2 | 1/2005 | Cristiano et al. | |
| 6,916,857 B2 | 7/2005 | Won et al. | |
| 6,924,370 B2 | 8/2005 | Chudzik et al. | |
| 7,025,990 B2 | 4/2006 | Sawhney | |
| 7,030,097 B1 | 4/2006 | Saltzman | |
| 7,094,418 B2 | 8/2006 | Chudzik et al. | |
| 7,138,132 B2 | 11/2006 | Won et al. | |
| 7,247,288 B2 * | 7/2007 | Kumta et al. | 423/308 |
| 7,514,530 B2 | 4/2009 | Divita et al. | |
| 7,531,191 B2 | 5/2009 | Zion et al. | |
| 7,638,344 B2 | 12/2009 | Slager et al. | |
| 7,759,316 B2 | 7/2010 | Kitamura et al. | |
| 2001/0018072 A1 | 8/2001 | Unger | |
| 2003/0014036 A1 | 1/2003 | Varner et al. | |
| 2003/0218130 A1 | 11/2003 | Boschetti et al. | |
| 2004/0062778 A1 | 4/2004 | Shefer et al. | |
| 2004/0091605 A1 | 5/2004 | Bayer et al. | |
| 2004/0133155 A1 | 7/2004 | Varner et al. | |
| 2005/0019371 A1 | 1/2005 | Anderson et al. | |
| 2005/0025797 A1 | 2/2005 | Wang et al. | |
| 2005/0059956 A1 | 3/2005 | Varner et al. | |
| 2005/0143363 A1 | 6/2005 | De Juan et al. | |
| 2005/0255142 A1 | 11/2005 | Chudzik | |
| 2005/0271703 A1 | 12/2005 | Anderson et al. | |
| 2005/0271706 A1 | 12/2005 | Anderson et al. | |
| 2005/0276837 A1 | 12/2005 | Anderson et al. | |
| 2005/0281781 A1 | 12/2005 | Ostroff | |
| 2005/0281863 A1 | 12/2005 | Anderson et al. | |
| 2005/0287188 A1 | 12/2005 | Anderson et al. | |
| 2006/0036029 A1 | 2/2006 | Tomko et al. | |
| 2006/0110428 A1 | 5/2006 | deJuan et al. | |
| 2006/0286071 A1 | 12/2006 | Epstein et al. | |
| 2007/0026037 A1 | 2/2007 | Kloke et al. | |
| 2007/0065481 A1 | 3/2007 | Chudzik et al. | |
| 2007/0065482 A1 | 3/2007 | Chudzik et al. | |
| 2007/0065483 A1 | 3/2007 | Chudzik et al. | |
| 2007/0065484 A1 | 3/2007 | Chudzik et al. | |
| 2007/0128343 A1 | 6/2007 | Chappa | |
| 2007/0155906 A1 | 7/2007 | Hissink et al. | |
| 2007/0218102 A1 | 9/2007 | Chudzik et al. | |
| 2007/0224247 A1 | 9/2007 | Chudzik et al. | |
| 2007/0260054 A1 | 11/2007 | Chudzik | |
| 2008/0038354 A1 | 2/2008 | Slager et al. | |
| 2008/0089923 A1 | 4/2008 | Burkstrand | |
| 2008/0154241 A1 | 6/2008 | Burkstrand et al. | |
| 2008/0234183 A1 | 9/2008 | Hallbrink et al. | |
| 2009/0093026 A1 | 4/2009 | Dowdy et al. | |
| 2009/0124535 A1 | 5/2009 | Markland et al. | |
| 2009/0186059 A1 | 7/2009 | Johnson et al. | |
| 2009/0214619 A1 | 8/2009 | Reiff | |
| 2009/0280181 A1 | 11/2009 | Slager | |
| 2009/0304798 A1 | 12/2009 | Davis | |
| 2010/0226960 A1 | 9/2010 | Chudzik et al. | |
| 2011/0159098 A1 | 6/2011 | Slager | |
| 2011/0319473 A1 | 12/2011 | Mcgonigle et al. | |
| 2012/0190726 A1 | 7/2012 | Slager | |

FOREIGN PATENT DOCUMENTS

| | | |
|---|---|---|
| WO | 9309176 | 5/1993 |
| WO | 9704011 | 2/1997 |
| WO | WO-00/04876 | 2/2000 |
| WO | 0012616 | 3/2000 |
| WO | 00/41647 | 7/2000 |
| WO | WO-00/50050 | 8/2000 |
| WO | 2004009664 | 1/2004 |
| WO | 2005034875 | 4/2005 |
| WO | 2005113034 | 12/2005 |
| WO | WO-2005112894 | 12/2005 |
| WO | 2006071110 | 7/2006 |
| WO | 2007/084418 | 7/2007 |
| WO | WO-2007084418 | 7/2007 |
| WO | 2008/003043 | 1/2008 |
| WO | WO-2008019346 | 2/2008 |
| WO | WO-2009/005709 | 1/2009 |
| WO | 2009/091812 | 7/2009 |
| WO | 2009/137689 | 11/2009 |
| WO | 2012006169 | 1/2012 |

OTHER PUBLICATIONS

Lee et al., "Solid Polymeric Microparticles Enhance the Delivery of siRNA to Macrophages in Vivo", Nucleic Acids Research, 1-10 Nucleic Acids Research Advance Access, Sep. 25, 2009, pp. 1-10.

Bergen et al., "Nonviral Approaches for Neuronal Delivery of Nucleic Acids", Pharmaceutical Research, vol. 25, No. 5 (May 2008), 983-998.

Akhtar et al., "Nonviral Delivery of Synthetic siRNAs in Vivo", The Journal of Clinical Investigation, vol. 117, No. 12 http://www.jci.org Dec. 2007, 3623-3632.

Adami et al., "Metabolic Stability of Glutaraldehyde Cross-linked Peptide DNA Condensates", J. Pharm. Sci., 88(8), 739-46 Abstract only (Aug. 1999).

Meade et al., "Enhancing the Cellular Uptake of siRNA Duplexes Following Noncovalent Packaging with Protein Transduction Domain Peptides", Adv Drug Deliv Rev, 60(4-5): 530-536, Abstract Howard Hughes Medical Institute, Author Manuscript Mar. 1, 2008, pp. 1-12.

Noguchi et al., "Protein Transduction Technology: A Novel Therapeutic Perspective", Acta Med. Okayama, vol. 60, No. 1 http://www.lib.okayama-u.ac.jp/www/acta/ pp. 1-11 (2006).

Quick et al., "DNA Delivery from Photocrosslinked PEG Hydrogels: Encapsulation Efficiency, Release Profiles, and DNA Quality", J. Control. Release, vol. 96, No. 2, pp. 341-351 (2004).

Brandup et al., "Polymer Handbook", 4th ed. John Wiley & Sons, N.Y. Beginning at VII, pp. 675-710 (1999).

Remaut et al., "Nucleic Acid Delivery: Where Material Sciences and Bio-Sciences Meet", Materials Science and Engineering R: Reports, Elsevier, Nov. 7, 2007, vol. 58, No. 3-5, pp. 117-161.

Boussif et al., "A Versatile Vector for Gene and Oligonucleotide Transfer into Cells in Culture and in Vivo: Polyethylenimine", Proc. Natl. Acad. Sci. USA, 92:7297-7301 (1995).

Schiffelers et al., "Cancer siRNA Therapy by Tumor Selective Delivery with Ligand-Targeted Sterically Stabilized Nanoparticle", Nucleic Acids Research, 32(19):e149 (2004).

Pannier et al., "Controlled Release Systems for DNA Delivery", Molecular Therapy, 10(1):19-26 (2004).

Thomas et al., "Cross-linked Small Polyethylenimines: While Still Nontoxic, Deliver DNA Efficiently to Mammalian Cells in Vitro and in Vivo", Pharmaceutical Research, 22(3):373-380 (2005).

Luu et al., "Development of a Nanostructured DNA Delivery Scaffold Via Electrospinning of PLGA and PLA-PEG Block Copolymers", Journal of Controlled Release, 89:341-353 (2003).

Sullenger, "Emerging Clinical Applications of Nucleic Acids", The Journal of Clinical Investigation, 106(8):921-922 (2000).

Thomas et al., "Enhancing Polyethylenimine's Delivery of Plasmid DNA into Mammalian Cells", PNAS, 99(23):14640-14645 (2002).

(56) References Cited

OTHER PUBLICATIONS

Thomas et al., "Full Deacylation of Polyethylenimine Dramatically Boosts its Gene Delivery Efficiency and Specificity to mouse lung", PNAS, 102(16):5679-5684 (2005).
Jang, et al., "Gene Delivery from Polymer Scaffolds for Tissue Engineering", Expert Rev. Medical Devices, 1(1):127-138 (2004).
Kapoor, "How to Cross-link Proteins", Cellular, Molecular and Microbial Biology Division, University of Calgary, Jul. 27, 2005, pp. 1-6.
Mayer et al., "Expert Opin. Drug Deliv,", (2008), 5(10):1121-1138.
File History (partial) for related U.S. Appl. No. 12/353,792, "Devices and Methods for Elution of Nucleic Acid Delivery Complexes," (166 pages).
Final Office Action, for U.S. Appl. No. 12/968,365, dated Jan. 30, 2013, 9 pages.
International Preliminary Report on Patentability, from International Application No. PCT/US2009/030972, mailed Jul. 20, 2010, pp. 1-10.
International Search Report and Written Opinion, from International Application No. PCT/US2009/030972, mailed Apr. 7, 2010, pp. 1-16.
Non-Final Office Action, mailed Aug. 9, 2012 in U.S. Appl. No. 12/968,365, "Stabilization and Delivery of Nucleic Acid Complexes," (22 pages).
Davis, "Non-Viral Gene Delivery Systems", Current Opinion in Biotechnology, 13:128-131 (2002).
Thomas et al., "Non-Viral Gene Therapy: Polycation-Mediated DNA Delivery", Appl. Microbiol. Biotechnol., 62:27-34 (2003).
Wieland et al., "Non-Viral Vector Delivery from PEG-Hyaluroic Acid Hydrogels", Journal of Controlled Release, 120(3):233-241 (2007).
Moffatt et al., "PEGylated J591 mAb Loaded in PLGA-PEG-PLGA Tri-Block Copolymer for Targeted Delivery: In Vitro Evaluation in Human Prostrate Cancer Cells", International Journal of Pharmaceutics, 317:10-13 (2006).
Zaitsev et al., "Polyelectrolyte Nanoparticles Mediate Vascular Gene Delivery", Pharmaceutical Research, 21(9):1656-1661 (2004).
Lungwitz et al., "Polyethylenimine-Based Non-Viral Gene Delivery Systems", European Journal of Pharmaceutics and Biopharmaceutics, 60:247-266 (2005).
Carlisle et al., "Polymer-Coated Polyethylenimine/DNA Complexes Designed for Triggered Activation by intracellular reduction", The Journal of Gene Medicine, 6:337-344 (2004).
Putnam, "Polymers for Gene Delivery Across Length Scales", Nature Materials, 5:439-451 (2006).
Oh et al., "Prolonged Organ Retention and Safety of Plasmid DNA Administered in Polyethylenimine Complexes", Gene Therapy, 8:1587-1592 (2001).
Jewell et al., "Release of Plasmid DNA from Intravascular Stents Coated with Ultrathin Multilayered Polyelectrolyte Films", Biomacromolecules, 7:2483-2491 (2006).
Urban-Klein et al., "RNAi-Mediated Gene-Targeting Through Systemic Application of Polyethylenimine (PEI)-Complexed siRNA in vivo", Gene Therapy, 12:461-466 (2005).
Lucius et al., "Structure of Transfection-Active Histone H1/DNA Complexes", Molecular Biology Reports, 28:157-165 (2002).
Godbey et al., "Tracking the Intracellular Path of Poly(ethylenimine)/DNA Complexes for Gene Delivery", Proc. Natl. Acad. Sci. USA, 96:5177-5181 (1999).
Takahashi et al., "Transgene Delivery of Plasmid DNA to Smooth Muscle Cells and Macrophages from a Biostable Polymer-Coated Stent", Gene Therapy, 10:1471-1478 (2003).
Schiffelers et al., "Transporting Silence: Design of Carriers for siRNA to Angiogenic Endothelium", Journal of Controlled Release, 109:5-14 (2005).
Heath et al., "Varying Polymer Architecture to Deliver Drugs", The AAPS Journal, 9(2):E235-E240 (2007).
Andersen, O. M. et al., "Delivery of siRNA from Lyophlolized Polymeric Surfaces", Biomaterials, vol. 24, 2008, pp. 506-512 2008.
Artursson, Per et al., "Characterization of Polyacryl Starch Microparticles as Carriers for Proteins and Drugs", J Pharm Sci. Nov. 1984;73(11):1507-13.
Azevedo, Helena S. et al., "in Vitro Assessment of the Enzymatic Degradation of Several Starch Based Biomaterials", Biomacromolecules. Nov.-Dec. 2003;4(6):1703-12.
Corveleyn, S. et al., "Maltodextrins as lyoprtectants in the lyophilization of a model protein, LDH.", http://www.biomedsearch.com/nih/maltodextrins-as-lyoprotectants-in-lyophilization/8668 (Accessed May 24, 2010) (2 pages).
Final Office Action, for U.S. Appl. No. 12/968,365, mailed Jun. 6, 2014 (11 pages).
Final Office Action, from U.S. Appl. No. 13/335,724, mailed Feb. 24, 2014, 6 pages.
Gonnissen, Y. et al., "Effect of maltodextrin and superdisintegrant in directly compressible powder mixtures prepared via co-spray drying", European Journal of Pharmaceutics and Biopharmaceutics, vol. 68, issue 2 (Feb. 2008), p. 277-282.
Hinrichs, W L J. et al., "The choice of a suitable oligosaccharide to prevent aggregation of PEGylated nanoparticles during freeze thawing and freeze drying", International Journal of Pharmaceutics. Elsevier BV. NL. vol. 311. No. 1-2, Mar. 27, 2006. pp. 237-244. XP027972683. ISSN: 0378-5173 [retrieved on Mar. 27, 2006] abstract p. 238. left-hand column. last paragraph—p. 239. right-han, 238-239.
Hinrichs, W.L.J. et al., "Inulin is a promising cryo—and lyoprotectant for PEGylated lipoplexes", Journal of COntrolled Release, vol. 103, Issue 2, Mar. 21, 2005, pp. 465-479.
Hirsch-Lerner, D. et al., "Effect of "helper lipid" on lipoplex electrostatics.", Biochim Biophys Acta. Aug. 15, 2005;1714(2):71-84.
Hoare, Todd R. et al., "Hydrogels in drug deliver: Progress and challenges", ScienceDirect, Polymer 49 (2008) p. 1993-2007.
International Preliminary Report on Patentability, for PCT/US2011/042398, mailed Jan. 17, 2013, (8 pages).
Jantas, R., "Synthesis and Characterization of Acryloyloxystarch", Journal of Applied Polymer Science vol. 65, Issue 11, pp. 2123-2129, Sep. 12, 1997.
Maclachlan, Ian, "Liposomal Formulations for Nucleic Acid Delivery", Antisense Drug Technologies: Principles, Strategies, and Applications, Second Edition, Taylor & Francis Group, L.L.C., (2007), pp. 237-270.
Maitani, Y et al., "Effect of sugars on storage stability of lyophilized liposome/DNA complexes with high transfection efficiency", International Journal of Pharmaceutics. Elsevier BV, NL. vol. 356. No. 1-2. May 22, 2008. pp. 69-75. XP022625172, ISSN: 0378-5173. 001: 10.1016/J.IJPHARM.2007.12.033 [retrieved on Dec. 31, 2007] abstract p. 70. left-hand column. para, 70-71.
Non-Final Office Action, from U.S. Appl. No. 13/335,724, mailed Aug. 23, 2013, 24 pages.
"Non-Final Office Action", mailed Nov. 23, 2012 in co-pending U.S. Appl. No. 13/171,171, "Compositions and Methods for Enhancement of Nucleic Acid Delivery," (10 pages)., 10.
"Notice of Allowance", for U.S. Appl. No. 13/335,724, mailed Jun. 6, 2014 (5 pages).
Odian, George, "Principles of Polymerization", Second Edition, John Wiley & Sons, (1981), pp. 201-204.
PCT International Search Report and Written Opinion from International, Application No. PCT/US2011/042398, corresponding to U.S. Patent, mailed Jul. 30, 2012, pp. 1-5, 1-5.
"Restriction Requirement Received", mailed Aug. 22, 2012 in co-pending U.S. Appl. No. 13/171,171, "Compositions and Methods for Enhancement of Nucleic Acid Delivery," (12 pages)., 12 pages.
Seville, P C. et al., "Preparation of Dry Powder Dispersions for Non-Viral Gene Delivery by Freeze-Drying and Spray-Drying", The Journal of Gene Medicine, vol. 4, 2002, pp. 428-437.
The Science and Practice of Pharmacy, Remington, 21st Edition, Copyright 2006 Lawrence & Hess.
Tseng, et al., "Advanced Drug Delivery Reviews", (2009), vol. 61, pp. 721-731.
Vintiloiu, Anda et al., "Organongels and their use in drug deliver—a review", http://www.sciencedirect.com/science?_ob=ArticleURL_udi=B6T3D-4R3351D1—use (3 pages) (2007).

(56) References Cited

OTHER PUBLICATIONS

Yadava, Preeti et al., "Effect of Lyophilization and Freeze-Thawing on the Stability of siRNA-liposome Complexes", AAPS PharmSciTech, vol. 9, 2008, pp. 335-341.

"Office Action", for Canadian Patent Application No. 2,723,192, mailed Oct. 7, 2014 (2 pages).

"Second Office Action", for Japanese Patent Application No. 2011508670, mailed Aug. 26, 2014 (7 pages) with English translation.

* cited by examiner

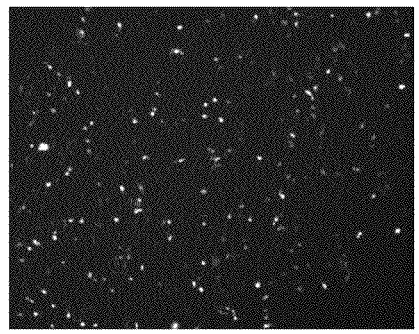
FIG. 7
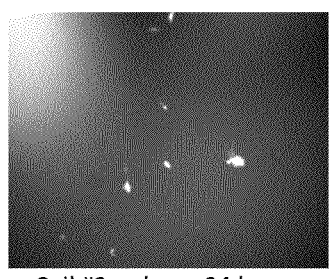 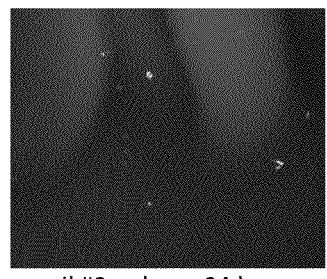
Coil #2, release 24 hours     coil #3, release 24 hours
FIGS. 8A-8B

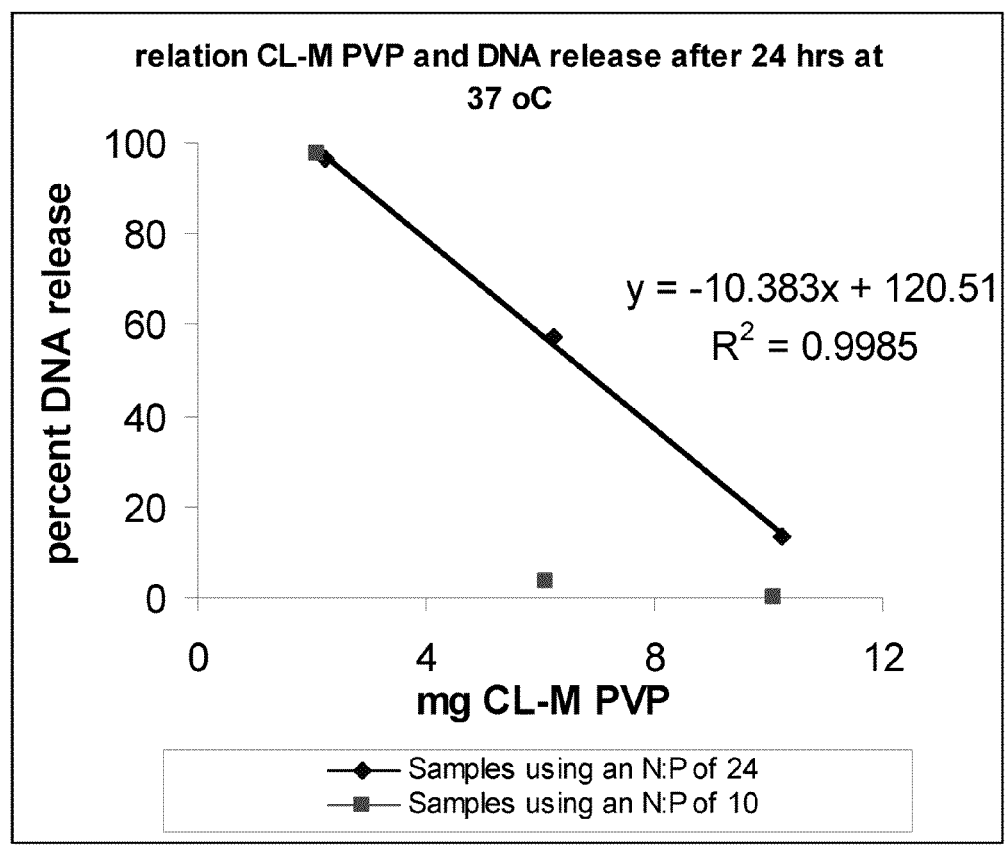
FIG. IIA

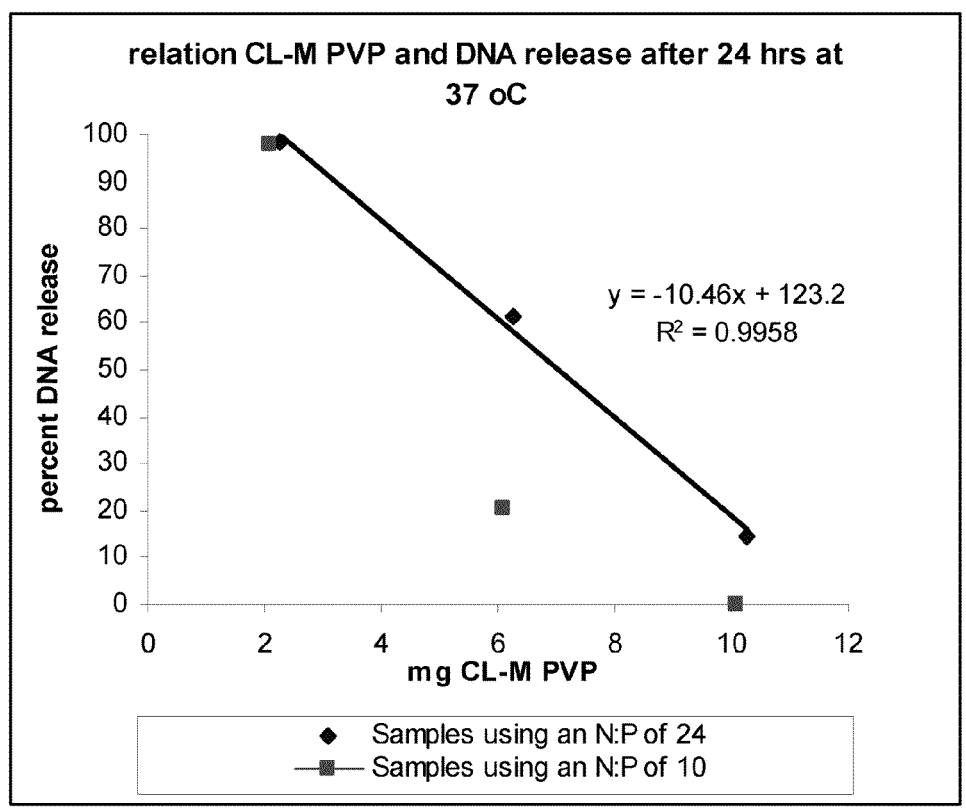
FIG. IIB

DEVICE COATED WITH GLYCOGEN PARTICLES COMPRISING NUCLEIC ACID COMPLEXES

This application claims the benefit of U.S. Provisional Application No. 61/051,041, filed May 7, 2008, the contents of which are herein incorporated by reference.

FIELD OF THE INVENTION

The present invention relates to devices and methods for the release of active agents. More specifically, the present invention relates to devices and methods for the release of nucleic acid complexes from particles.

BACKGROUND OF THE INVENTION

One promising approach to the treatment of various medical conditions is the administration of nucleic acids as therapeutic agents. By way of example, this approach can include the administration of RNA, DNA, siRNA, miRNA, piRNA, shRNA, antisense nucleic acids, aptamers, ribozymes, catalytic DNA and the like.

In order to mediate an effect on a target cell, a nucleic acid based active agent must generally be delivered to an appropriate target cell, taken up by the cell, released from an endosome, and transported to the nucleus or cytoplasm (intracellular trafficking), among other steps. As such, successful treatment with nucleic acids depends upon site-specific delivery, stability during the delivery phase, and a substantial degree of biological activity within target cells. For various reasons, these steps can be difficult to achieve. As one example, nucleic acids are readily degraded by enzymes in the in vivo environment.

Accordingly, a need remains for devices that can deliver therapeutic nucleic acids to a target tissue and methods of making and using the same.

SUMMARY OF THE INVENTION

Embodiments of the invention include particles with nucleic acid complexes, medical devices including the same, and related methods. In an embodiment, the invention includes a method of forming particles with nucleic acid complexes including contacting nucleic acids with cationic carrier agents to form nucleic acid complexes, and absorbing the nucleic acid complexes to porous particles, the particles having an average diameter of less than about 100 μm.

In an embodiment, the invention includes a method of forming particles with nucleic acid complexes. The method can include contacting nucleic acids with cationic carrier agents to form nucleic acid complexes, contacting the nucleic acid complexes with a polymer, and cross-linking the polymer.

In an embodiment, the invention can include a method of forming particles with nucleic acid complexes including contacting nucleic acids with cationic carrier agents to form nucleic acid complexes, and contacting the nucleic acid complexes with a solution comprising a peptide, the nucleic acid complexes acting as a nucleating agent for the peptide.

In an embodiment, the invention can include a method of making a medical device. The method can include contacting nucleic acids with cationic carrier agents to form nucleic acid complexes, adsorbing the nucleic acid complexes to porous particles to form nucleic acid complex containing particles, mixing the nucleic acid complex containing particles with a polymer solution to form a coating mixture, and applying the coating mixture to a substrate.

In an embodiment, the invention can include a method of making a medical device. The method can include contacting nucleic acids with cationic carrier agents to form nucleic acid complexes, combining the nucleic acid complexes with a material to form nucleic acid complex containing particles in situ, mixing the nucleic acid complex particles with a polymer solution to form a coating mixture, and applying the coating mixture to a substrate.

In an embodiment, the invention can include an implantable medical device including a substrate, an elution control matrix disposed on the substrate, a plurality of particles disposed within the elution control matrix, and a plurality of nucleic acid complexes disposed within the particles, the nucleic acid complexes comprising a nucleic acid and a cationic carrier agent.

The above summary of the present invention is not intended to describe each discussed embodiment of the present invention. This is the purpose of the figures and the detailed description that follows.

BRIEF DESCRIPTION OF THE FIGURES

The invention may be more completely understood in connection with the following drawings, in which:

FIG. 7 is an image of HEK293 cells taken using fluorescence microscopy.

FIGS. 8A-8B are images of HEK293 cells taken using fluorescence microscopy.

FIGS. 11A-11B are graphs showing release of DNA as a function of milligrams of PVP particles.

Figure 1:
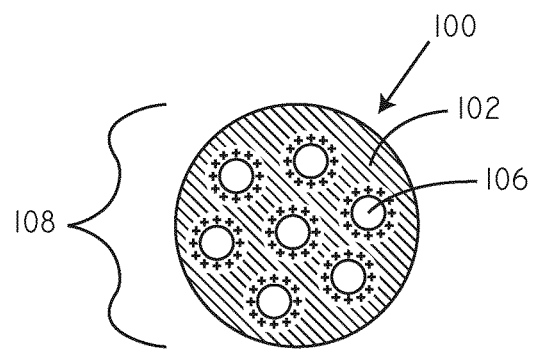
FIG. 1 is a cross-sectional schematic view of a particle including nucleic acid complexes in accordance with an embodiment herein.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

As used herein, the term "complex" shall refer to a chemical association of two or more chemical species through non-covalent bonds.

One approach to maintaining the activity of nucleic acid-based therapeutic agents is to complex the nucleic acids with a delivery agent prior to administration to a mammalian subject. By way of example, nucleic acids (having a net negative charge) can be complexed to carrier agents having a net positive charge, such as polyethylenimine, in order to prevent degradation during the delivery phase and enhance cell entry. These nucleic acid/carrier complexes are sometimes referred to as polyplexes or nucleic acid complexes (in some contexts these complexes have also been referred to as nucleic acid delivery particles, though that use of the term "particle" is distinct from the particles including nucleic acid complexes described herein). While the use of polyplexes can aid in preserving the activity of the nucleic acid during the delivery phase, it does not address the issue of controlled release of the nucleic acid.

Elution control matrices are used to provide controlled release of some types of active agents. However, delivery of nucleic acid complexes from an elution control matrix, such as an elution control coating, can present a particular challenge because they can dissociate or otherwise become inactivated under the conditions typically used for coating formation. For example, nucleic acid complexes may become inactivated or otherwise damaged by organic solvents commonly used to apply polymeric elution control coatings.

Embodiments of the invention can include methods for administering nucleic acid complexes involving disposing the complexes within particles and then incorporating the particles into devices and/or coatings. After the nucleic acid complexes are disposed within particles, they are more robust and less subject to degradation during subsequent processing. Yet the nucleic acid complexes disposed within particles can retain their activity and, as shown the examples below, can be used successfully to transfect target cells. In some embodiments, the nucleic acid complexes disposed within particles can even retain their activity despite being suspended in an organic solvent. The particles into which the nucleic acid complexes are disposed can either be preformed, such as in the context of porous ceramic particles, or they can be formed in situ from a mixture including nucleic acid complexes and at least one other component such as a polymeric excipient. Polymeric excipients can include, but are not limited to, peptides and polysaccharides. Aspects of exemplary embodiments will now be described in greater detail.

Referring now to FIG. 1, a cross-sectional schematic view of a particle 100 including nucleic acid complexes is shown (not to scale). The particle 100 can include a particle material 102 and one or more nucleic acid complexes 106 within the particle material 102. The particle material can be polymeric (including cross-linked polymers), ceramic, metallic, or the like. Specific examples can include, but are not limited to, kaolin, cross-linked polyvinylpyrrolidone, or cross-linked methacrylate maltodextrin The particle material can be preformed and then nucleic acid complexes can be added to it. Alternatively, the particle material can be formed in situ around the nucleic acid complexes. Specific examples of particle materials are described in greater detail below. The nucleic acid complexes can include a nucleic acid and a cationic carrier agent. Further details regarding exemplary nucleic acid complexes are provided below. The particle 100 can have a diameter 108 between about 1 µm and about 50 µm. Though the particle 100 shown in FIG. 1 is spherical in cross-section, it will be appreciated that embodiments of the invention can include particles with different shapes including irregular shapes.

In some embodiments, such as where the particle is formed through a phase separation technique, residual amounts of the amphiphilic polymer used to trigger phase separation may remain in the particles. In some embodiments, the amount of the amphiphilic polymer left in the particles is less than about 5 percent by weight. In some embodiments, it is less than about 2 percent by weight. In some embodiments, it is greater than 0 percent by weight. In some embodiments, it is between 0 percent by weight and 5 percent by weight.

Figure 2:
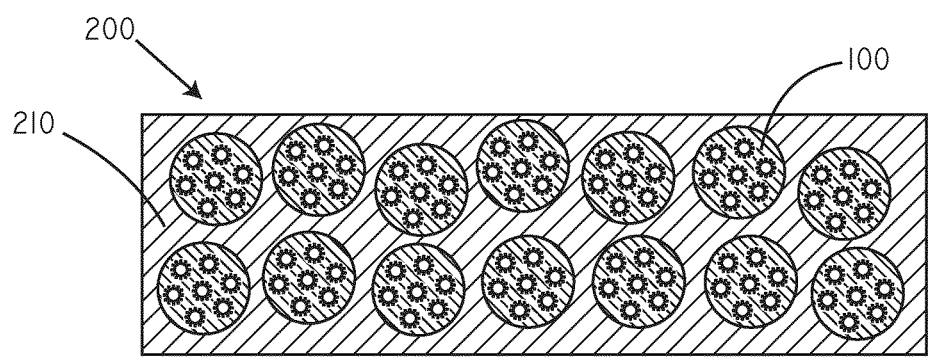
FIG. 2 is a cross-sectional schematic view of an active agent delivery device in accordance with an embodiment herein.

In accordance with various embodiments herein, particles containing nucleic acid complexes can be incorporated within active agent elution control matrices (or controlled release matrices). Referring now to FIG. 2, a plurality of particles 100 are shown disposed within an elution control matrix 210 forming an active agent delivery device 200. The elution control matrix 210 can be made of a material that allows for the elution of the nucleic acid complexes within the particles 100 to the outside of the elution control matrix 210. The elution control matrix 210 can include various materials such as various polymers. In some embodiments, the elution control matrix 210 can include non-degradable polymers. Exemplary non-degradable polymers are described in greater detail below. In some embodiments, the elution control matrix 210 can include degradable polymers. Exemplary degradable polymers are described in greater detail below. In some embodiments, the elution control matrix 210 can include both degradable and non-degradable polymers. The elution control matrix 210 can be deposited using various techniques. By way of example, spray deposition, dip coating, brush coating, printing, casting, and the like. In some embodiments, such as to facilitate spray deposition, the particles 100 may be suspended in an organic solvent prior to deposition. By way of example, the particles 100 may be suspended in an organic solvent along with polymers of the elution control matrix 210 prior to deposition. In FIG. 2, the active agent delivery device 200 is shown in a substantially planar configuration. However, it will be appreciated that the device 200 can take on many different forms including a filament, a cylinder, an irregular shape, or the like.

Figure 3:
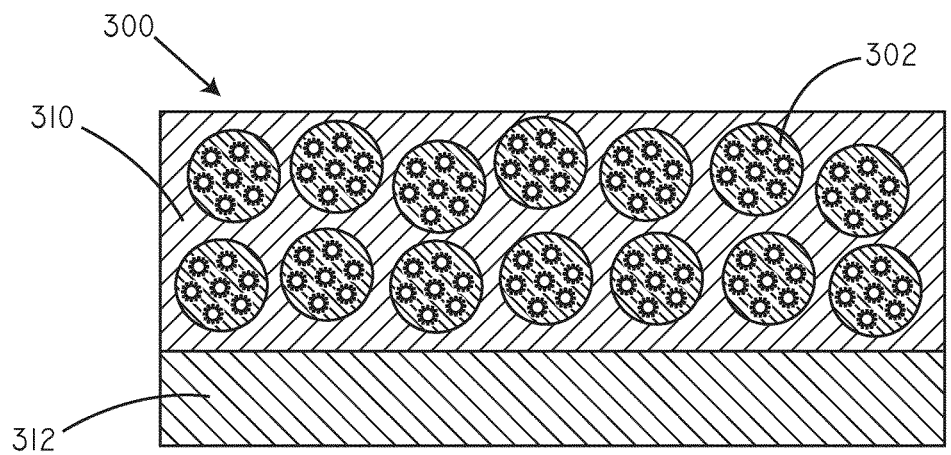
FIG. 3 is a cross-sectional schematic view of an active agent delivery device in accordance with an embodiment herein.

In some embodiments, an elution control matrix including particles containing nucleic acid complexes can be disposed on a substrate of a medical device. By way of example, such an elution control matrix can be disposed upon a metal stent. Further examples of medical devices included herein are provided below. Referring now to FIG. 3, a device 300 is shown including an elution control matrix 310 with particles 302 including nucleic acid complexes, wherein the elution control matrix 310 is disposed upon a substrate 312. The substrate 312 can include various types of materials including polymers, metals, ceramics, and the like. Further examples of substrate materials are described below. The substrate 312 as illustrated can represent a portion of a medical device.

Particles containing nucleic acid complexes can be formed in various ways. As described above, in some embodiments, a particle material is preformed and the nucleic acid complexes are added to, or absorbed to, the particle material. In other embodiments, the particle material is formed in situ around the nucleic acid complexes. Various techniques can be used to form a particle material around a nucleic acid complex. In some embodiments, the particle material can be polymeric and a cross-linking step can be performed to cross link the polymer after it is disposed around nucleic acid complexes. Cross-linking can be initiated through various techniques know to those of skill in the art including photo-initiation and redox reaction initiation.

In some embodiments, a nucleic acid complex can effectively serve as a nucleating agent and material to form a particle can be deposited around the nucleic acid complex. By way of example, proteins (such as Fab fragments) can be formed into a particle using a nucleic acid complex with techniques such as phase separation techniques. In such an embodiment, the protein or peptide can serve as a polymeric excipient that undergoes phase separation. An example of this approach is shown with respect to example 3 below. In such approaches, the peptide can be dissolved in solution at a concentration sufficient for the formation of peptide nuclei when a nucleating agent is added to the peptide solution. In many preparations, the concentration of peptide in solution is generally at a concentration of about 10 mg/mL or greater. However if a chosen peptide is easily coalesced with the nucleating agent to form nuclei, lower concentrations of peptide may be used. In some specific modes of practice, the peptide is an antibody or Fab fragment, which is in solution at a concentration in the range of about 10 mg/mL to about 50 mg/mL, and more specifically in the range of 15 mg/mL to about 20 mg/mL.

It will be appreciated that other components can also serve as a polymeric excipient that undergoes phase separation besides peptides. By way of example, polymeric excipients can also include polysaccharides. An exemplary polysaccharide can include, but is not limited to, glycogen.

Figure 4:
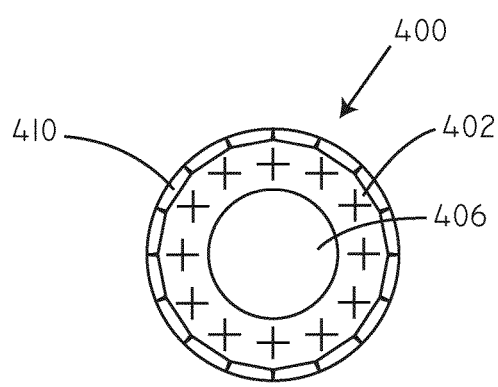
FIG. 4 is a cross-sectional schematic view of a particle including a nucleic acid complex in accordance with an embodiment herein.

Referring now to FIG. 4, a schematic view of a particle 400 including a nucleic acid complex 406 is shown. The nucleic acid complex 406 includes a nucleic acid and a cationic carrier agent. The nucleic acid complex includes a plurality of positively charged groups 402 on its outer surface (conceptually illustrated here for purposes of explanation). A layer 410 of a material, such as a protein, can be disposed around the nucleic acid complex 406. In some embodiments, the layer 410 can also include other types of materials including polymers, carbohydrates, and the like.

It will be appreciated that phase separation techniques can include mixing a phase separation agent into a solution containing the component materials for forming particles. The phase separation agent can be an amphiphilic compound. The amphiphilic reagent can be selected from polymeric and non-polymeric amphiphilic materials. In some aspects of the invention, the amphiphilic reagent is an amphiphilic polymer. Exemplary amphiphilic polymers and compounds include poly(ethyleneglycol) (PEG) and PEG copolymers, tetraethylene glycol, triethylene glycol, trimethylolpropane ethoxylate, and pentaeerythritol ethoxylate, polyvinylpyrrolidone (PVP) and PVP copolymers, dextran, Pluronic™, polyacrylic acid, polyacrylamide, polyvinyl pyridine, polylysine, polyarginine, PEG sulfonates, fatty quaternary amines, fatty sulfonates, fatty acids, dextran, dextrin, and cyclodextrin. The amphiphilic polymer can also be copolymers of hydrophilic and hydrophobic polymeric blocks.

In some aspects, a concentrated solution of an amphiphilic reagent (such as an amphiphilic polymer) is prepared and then added to the solution containing the component materials for forming particles. In many modes of practice, the amphiphilic reagent is added to a solution so that the final concentration of the amphiphilic reagent is about 1% (w/v) or greater. In some embodiments, the final concentration of the amphiphilic reagent is in the range of about 2.5% (w/v) to about 12.5% (w/v), or more specifically about 5% (w/v) to about 10% (w/v). For example, an amphiphilic reagent such as PEG can be used in the amount of about 7.5%.

Nucleic Acid Complexes

Nucleic acid complexes used with various embodiments can include a nucleic acid as an active agent and a carrier agent complexed to the nucleic acid. Carrier agents used with embodiments of the invention can include those compounds that can be complexed with nucleic acids in order to preserve the activity of the nucleic acids during the manufacturing and delivery processes.

Exemplary classes of suitable carrier agents can include cationic compounds (compounds having a net positive charge) and charge neutral compounds. By way of example, suitable carrier agents can include cationic polymers and cationic lipids. Suitable cationic carrier agents can also include polycation containing cyclodextrin, histones, cationized human serum albumin, aminopolysaccharides such as chitosan, peptides such as poly-L-lysine, poly-L-ornithine, and poly(4-hydroxy-L-proline ester, and polyamines such as polyethylenimine (PEI), polypropylenimine, polyamidoamine dendrimers, and poly(beta-aminoesters). Other carrier agents can include solid nucleic acid lipid nanoparticles (SNALPs), liposomes, polyvinyl pyrrolidone (PVP), and the like. Additionally, carriers may also be conjugated to molecules which allow them to target specific cell types. Examples of targeting agents include antibodies and peptides which recognize and bind to specific cell surface molecules.

For example, in one mode of practice, a polyplex is prepared by combining PEI with a nucleic acid. As a general matter, the PEI reagent provides a particular number of primary amino groups ("N") per weight unit, and the nucleic acid provides a particular number of charged phosphate groups ("P") per weight unit. The PEI and the nucleic acid can be combined to provide a desired N:P ratio. In some aspects the N:P ratio is in the range of about 10:1 to about 25:1.

In some embodiments, nucleic acid delivery constructs used with embodiments of the invention can include peptides that facilitate delivery of a nucleic acid to a cell of interest. For example, exemplary peptides can associate with a nucleic acid and facilitate delivery of that nucleic acid to the cytoplasm of a cell. As used herein, the term "peptide" shall include any compound containing two or more amino-acid residues joined by amide bond(s) formed from the carboxyl group of one amino acid (residue) and the amino group of the next one. As such, peptides can include oligopeptides, polypeptides, proteins, and the like.

In some embodiments, nucleic acid delivery constructs used with embodiments of the invention can include peptides that have at least two domains, such as a cellular penetration domain and a nucleic acid binding domain. As used herein, the term "cellular penetration domain" shall refer to a region of a peptide molecule that functions to facilitate entry of the molecule into a cell. As used herein, the term "nucleic acid binding domain" shall refer to a region of a peptide molecule that functions to bind with nucleic acids.

It will be appreciated that many different peptides are contemplated herein. One exemplary peptide, known as MPG, is a 27 amino acid bipartite amphipathic peptide composed of a hydrophobic domain derived from HIV-1 gp41 protein and a basic domain from the nuclear localization sequence (NLS) of SV40 large T antigen (GALFLGFLGAAGSTMGAWSQPKKKRKV) (commercially available as the N-TER Nanoparticle siRNA Transfection System from Sigma-Aldrich, St. Louis, Mo.). Another exemplary peptide, known as MPGΔ$^{NLS}$, is also a 27 amino acid bipartite amphipathic peptide (GALFLGFLGAAGSTMGAWSQPKSKRKV). Other exemplary peptides can include poly-arginine fusion peptides. Still other exemplary peptides include those with protein transduction domains linked with a double-stranded RNA binding domain (PTD-DRBD peptides).

Nucleic acids used with embodiments of the invention can include various types of nucleic acids that can function to provide a therapeutic effect. Exemplary types of nucleic acids can include, but are not limited to, ribonucleic acids (RNA), deoxyribonucleic acids (DNA), small interfering RNA (siRNA), micro RNA (miRNA), piwi-interacting RNA (piRNA), short hairpin RNA (shRNA), antisense nucleic acids, aptamers, ribozymes, locked nucleic acids and catalytic DNA.

Nucleic acid delivery complexes can be formed from carrier agents and nucleic acids through various processes. In some cases, for example, a cationic carrier agent interacts with an anionic nucleic acid molecule and condenses into a compact, ordered complex. As such, in some embodiments, the nucleic acid can simply be contacted with the cationic carrier agent in order to form nucleic acid delivery complexes.

Polymers

Polymers can be included as a material forming a particle in which nucleic acid complexes are disposed. Examples of polymers that can be used to form a particle that can include nucleic acids include ethylene vinyl alcohol copolymer; poly (hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether esters) (e.g., PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrilestyrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

Polymers can also be included in various embodiments as part of an elution control matrix. Many different types of polymers can be used for this purpose. Specific examples of polymers that can be used to form an elution control matrix are described below.

Degradable Polymers

Degradable polymers can be in conjunction with some embodiments herein. By way of example, in some embodiments degradable polymers can be included in a particle that contains nucleic acid complexes. In some embodiments, degradable polymers can be included in an elution control matrix that includes particles with nucleic acid complexes. Degradable polymers used with embodiments of the invention can include both natural or synthetic polymers. Examples of degradable polymers can include those with hydrolytically unstable linkages in the polymeric backbone. Degradable polymers of the invention can include both those with bulk erosion characteristics and those with surface erosion characteristics.

While not intending to be bound by theory, the use of degradable polyesters can be advantageous in the context of providing controlled release of nucleic acid complexes because release can be mediated by degradation of the matrix in addition to diffusion through the matrix.

Synthetic degradable polymers can include: degradable polyesters (such as poly(glycolic acid), poly(lactic acid), poly (lactic-co-glycolic acid), poly(dioxanone), polylactones (e.g., poly(caprolactone)), poly(3-hydroxybutyrate), poly(3-hydroxyvalerate), poly(valerolactone), poly(tartronic acid), poly(β-malonic acid), poly(propylene fumarate)); degradable polyesteramides; degradable polyanhydrides (such as poly(sebacic acid), poly(1,6-bis(carboxyphenoxy)hexane, poly(1,3-bis(carboxyphenoxy)propane); degradable polycarbonates (such as tyrosine-based polycarbonates); degradable polyiminocarbonates; degradable polyarylates (such as tyrosine-based polyarylates); degradable polyorthoesters; degradable polyurethanes; degradable polyphosphazenes; and copolymers thereof.

Natural or naturally-based degradable polymers can include polysaccharides and modified polysaccharides such as starch, cellulose, chitin, chitosan, and copolymers thereof.

Specific examples of degradable polymers include poly (ether ester) multiblock copolymers based on poly(ethylene glycol) (PEG) and poly(butylene terephthalate) that can be described by the following general structure:

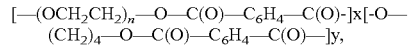

$[-(OCH_2CH_2)_n-O-C(O)-C_6H_4-C(O)-]x[-O-(CH_2)_4-O-C(O)-C_6H_4-C(O)-]y$, where $-C_6H_4-$ designates the divalent aromatic ring residue from each esterified molecule of terephthalic acid, n represents the number of ethylene oxide units in each hydrophilic PEG block, x represents the number of hydrophilic blocks in the copolymer, and y represents the number of hydrophobic blocks in the copolymer. The subscript "n" can be selected such that the molecular weight of the PEG block is between about 300 and about 4000. The block copolymer can be engineered to provide a wide array of physical characteristics (e.g., hydrophilicity, adherence, strength, malleability, degradability, durability, flexibility) and active agent release characteristics (e.g., through controlled polymer degradation and swelling) by varying the values of n, x and y in the copolymer structure. Such degradable polymers can specifically include those described in U.S. Pat. No. 5,980,948, the content of which is herein incorporated by reference in its entirety.

Degradable polyesteramides can include those formed from the monomers OH-x-OH, z, and COOH-y-COOH, wherein x is alkyl, y is alkyl, and z is leucine or phenylalanine. Such degradable polyesteramides can specifically include those described in U.S. Pat. No. 6,703,040, the content of which is herein incorporated by reference in its entirety.

Degradable polymeric materials can also be selected from: (a) non-peptide polyamino polymers; (b) polyiminocarbonates; (c) amino acid-derived polycarbonates and polyarylates; and (d) poly(alkylene oxide) polymers.

In an embodiment, the degradable polymeric material is composed of a non-peptide polyamino acid polymer. Exemplary non-peptide polyamino acid polymers are described, for example, in U.S. Pat. No. 4,638,045 ("Non-Peptide Polyamino Acid Bioerodible Polymers," Jan. 20, 1987). Generally speaking, these polymeric materials are derived from monomers, including two or three amino acid units having one of the following two structures illustrated below:

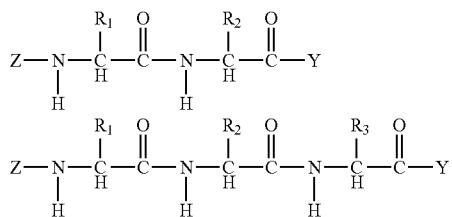

wherein the monomer units are joined via hydrolytically labile bonds at not less than one of the side groups $R_1$, $R_2$, and $R_3$, and where $R_1$, $R_2$, $R_3$ are the side chains of naturally occurring amino acids; Z is any desirable amine protecting group or hydrogen; and Y is any desirable carboxyl protecting group or hydroxyl. Each monomer unit comprises naturally occurring amino acids that are then polymerized as monomer units via linkages other than by the amide or "peptide" bond. The monomer units can be composed of two or three amino acids united through a peptide bond and thus comprise dipeptides or tripeptides. Regardless of the precise composition of the monomer unit, all are polymerized by hydrolytically labile bonds via their respective side chains rather than via the amino and carboxyl groups forming the amide bond typical of polypeptide chains. Such polymer compositions are non-toxic, are degradable, and can provide zero-order release kinetics for the delivery of active agents in a variety of therapeutic applications. According to these aspects, the amino acids are selected from naturally occurring L-alpha amino acids, including alanine, valine, leucine, isoleucine, proline, serine, threonine, aspartic acid, glutamic acid, asparagine, glutamine, lysine, hydroxylysine, arginine, hydroxyproline, methionine, cysteine, cystine, phenylalanine, tyrosine, tryptophan, histidine, citrulline, ornithine, lanthionine, hypoglycin A, β-alanine, γ-amino butyric acid, α aminoadipic acid, canavanine, venkolic acid, thiolhistidine, ergothioneine, dihydroxyphenylalanine, and other amino acids well recognized and characterized in protein chemistry.

Degradable polymers of the invention can also include polymerized polysaccharides such as those described in U.S. Publ. Pat. Application No. 2005/0255142, entitled "COATINGS FOR MEDICAL ARTICLES INCLUDING NATURAL BIODEGRADABLE POLYSACCHARIDES", U.S. Publ. Pat. Application No. 2007/0065481, entitled "COATINGS INCLUDING NATURAL BIODEGRADABLE POLYSACCHARIDES AND USES THEREOF", and in U.S. Publ. Pat. Application No. 20070218102, entitled "HYDROPHOBIC DERIVATIVES OF NATURAL BIODEGRADABLE POLYSACCHARIDES", all of which are herein incorporated by reference in their entirety.

Degradable polymers of the invention can also include dextran based polymers such as those described in U.S. Pat. No. 6,303,148, entitled "PROCESS FOR THE PREPARATION OF A CONTROLLED RELEASE SYSTEM", the content of which is herein incorporated by reference in its entirety. Exemplary dextran based degradable polymers including those available commercially under the trade name OCTODEX.

Degradable polymers of the invention can further include collagen/hyaluronic acid polymers.

Degradable polymers of the invention can include multi-block copolymers, comprising at least two hydrolysable segments derived from pre-polymers A and B, which segments are linked by a multi-functional chain-extender and are chosen from the pre-polymers A and B, and triblock copolymers ABA and BAB, wherein the multi-block copolymer is amorphous and has one or more glass transition temperatures (Tg) of at most 37° C. (Tg) at physiological (body) conditions. The pre-polymers A and B can be a hydrolysable polyester, polyetherester, polycarbonate, polyestercarbonate, polyanhydride or copolymers thereof, derived from cyclic monomers such as lactide (L,D or L/D), glycolide, ε-caprolactone, δ-valerolactone, trimethylene carbonate, tetramethylene carbonate, 1,5-dioxepane-2-one, 1,4-dioxane-2-one (para-dioxanone) or cyclic anhydrides (oxepane-2,7-dione). The composition of the pre-polymers may be chosen in such a way that the maximum glass transition temperature of the resulting copolymer is below 37° C. at body conditions. To fulfill the requirement of a Tg below 37° C., some of the above-mentioned monomers or combinations of monomers may be more preferred than others. This may by itself lower the Tg, or the pre-polymer is modified with a polyethylene glycol with sufficient molecular weight to lower the glass transition temperature of the copolymer. The degradable multi-block copolymers can include hydrolysable sequences being amorphous and the segments may be linked by a multifunctional chain-extender, the segments having different physical and degradation characteristics. For example, a multi-block co-polyester consisting of a glycolide-ε-caprolactone segment and a lactide-glycolide segment can be composed of two different polyester pre-polymers. By controlling the segment monomer composition, segment ratio and length, a variety of polymers with properties that can easily be tuned can be obtained. Such degradable multi-block copolymers can specifically include those described in U.S. Publ. App. No. 2007/0155906, the content of which is herein incorporated by reference in its entirety.

Non-Degradable Polymers

Non-degradable polymers can be in conjunction with some embodiments herein. By way of example, in some embodiments non-degradable polymers can be included in a particle that contains nucleic acid complexes. In some embodiments, non-degradable polymers can be included in an elution control matrix that includes particles with nucleic acid complexes. In an embodiment, the non-degradable polymer includes a plurality of polymers, including a first polymer and a second polymer. When the coating solution contains only one polymer, it can be either a first or second polymer as described herein. As used herein, the term "(meth)acrylate", when used in describing polymers, shall mean the form including the methyl group (methacrylate) or the form without the methyl group (acrylate).

First polymers of the invention can include a polymer selected from the group consisting of poly(alkyl(meth)acrylates) and poly(aromatic(meth)acrylates), where "(meth)" will be understood by those skilled in the art to include such molecules in either the acrylic and/or methacrylic form (corresponding to the acrylates and/or methacrylates, respectively). An exemplary first polymer is poly(n-butyl methacrylate) (pBMA). Such polymers are available commercially, e.g., from Aldrich, with molecular weights ranging from about 200,000 Daltons to about 320,000 Daltons, and with varying inherent viscosity, solubility, and form (e.g., as crystals or powder). In some embodiments, poly(n-butyl methacrylate) (PBMA) is used with a molecular weight of about 200,000 Daltons to about 300,000 Daltons.

Examples of suitable first polymers also include polymers selected from the group consisting of poly(aryl(meth)acrylates), poly(aralkyl(meth)acrylates), and poly(aryloxyalkyl (meth)acrylates). Such terms are used to describe polymeric structures wherein at least one carbon chain and at least one aromatic ring are combined with acrylic groups, typically esters, to provide a composition. In particular, exemplary polymeric structures include those with aryl groups having from 6 to 16 carbon atoms and with weight average molecular weights from about 50 to about 900 kilodaltons. Suitable poly(aralkyl(meth)acrylates), poly(arylalky(meth)acrylates) or poly(aryloxyalkyl(meth)acrylates) can be made from aromatic esters derived from alcohols also containing aromatic moieties. Examples of poly(aryl(meth)acrylates) include poly(9-anthracenyl methacrylate), poly(chlorophenylacrylate), poly(methacryloxy-2-hydroxybenzophenone), poly(methacryloxybenzotriazole), poly(naphthylacrylate) and -methacrylate), poly(4-nitrophenyl acrylate), poly(pentachloro(bromo, fluoro)acrylate) and -methacrylate), and poly(phenyl acrylate) and -methacrylate). Examples of poly(aralkyl(meth)acrylates) include poly(benzyl acrylate) and -methacrylate), poly(2-phenethyl acrylate) and -methacrylate, and poly(1-pyrenylmethyl methacrylate). Examples of poly(aryloxyalkyl(meth)acrylates) include poly(phenoxyethyl acrylate) and -methacrylate), and poly(polyethylene glycol phenyl ether acrylates) and -methacrylates with varying polyethylene glycol molecular weights.

Examples of suitable second polymers are available commercially and include poly(ethylene-co-vinyl acetate) (pEVA) having vinyl acetate concentrations of between about 10% and about 50% (12%, 14%, 18%, 25%, 33% versions are commercially available), in the form of beads, pellets, granules, etc. The pEVA co-polymers with lower percent vinyl acetate become increasingly insoluble in typical solvents, whereas those with higher percent vinyl acetate become decreasingly durable.

An exemplary polymer mixture includes mixtures of pBMA and pEVA. This mixture of polymers can be used with absolute polymer concentrations (i.e., the total combined concentrations of both polymers in the coating material), of between about 0.25 wt. % and about 99 wt. %. This mixture can also be used with individual polymer concentrations in the coating solution of between about 0.05 wt. % and about 99 wt. %. In one embodiment the polymer mixture includes pBMA with a molecular weight of from 100 kilodaltons to 900 kilodaltons and a pEVA copolymer with a vinyl acetate content of from 24 to 36 weight percent. In an embodiment the polymer mixture includes pBMA with a molecular weight of from 200 kilodaltons to 300 kilodaltons and a pEVA copolymer with a vinyl acetate content of from 24 to 36 weight percent. The concentration of the active agent or agents dissolved or suspended in the coating mixture can range from 0.01 to 99 percent, by weight, based on the weight of the final coating material.

Second polymers can also comprise one or more polymers selected from the group consisting of (i) poly(alkylene-co-alkyl(meth)acrylates, (ii) ethylene copolymers with other alkylenes, (iii) polybutenes, (iv) diolefin derived non-aromatic polymers and copolymers, (v) aromatic group-containing copolymers, and (vi) epichlorohydrin-containing polymers.

Poly(alkylene-co-alkyl(meth)acrylates) include those copolymers in which the alkyl groups are either linear or branched, and substituted or unsubstituted with non-interfering groups or atoms. Such alkyl groups can comprise from 1 to 8 carbon atoms, inclusive. Such alkyl groups can comprise from 1 to 4 carbon atoms, inclusive. In an embodiment, the alkyl group is methyl. In some embodiments, copolymers that include such alkyl groups can comprise from about 15% to about 80% (wt) of alkyl acrylate. When the alkyl group is methyl, the polymer contains from about 20% to about 40% methyl acrylate in some embodiments, and from about 25% to about 30% methyl acrylate in a particular embodiment. When the alkyl group is ethyl, the polymer contains from about 15% to about 40% ethyl acrylate in an embodiment, and when the alkyl group is butyl, the polymer contains from about 20% to about 40% butyl acrylate in an embodiment.

Alternatively, second polymers can comprise ethylene copolymers with other alkylenes, which in turn, can include straight and branched alkylenes, as well as substituted or unsubstituted alkylenes. Examples include copolymers prepared from alkylenes that comprise from 3 to 8 branched or linear carbon atoms, inclusive. In an embodiment, copolymers prepared from alkylene groups that comprise from 3 to 4 branched or linear carbon atoms, inclusive. In a particular embodiment, copolymers prepared from alkylene groups containing 3 carbon atoms (e.g., propene). By way of example, the other alkylene is a straight chain alkylene (e.g., 1-alkylene). Exemplary copolymers of this type can comprise from about 20% to about 90% (based on moles) of ethylene. In an embodiment, copolymers of this type comprise from about 35% to about 80% (mole) of ethylene. Such copolymers will have a molecular weight of between about 30 kilodaltons to about 500 kilodaltons. Exemplary copolymers are selected from the group consisting of poly(ethylene-co-propylene), poly(ethylene-co-1-butene), poly(ethylene-co-1-butene-co-1-hexene) and/or poly(ethylene-co-1-octene).

"Polybutenes" include polymers derived by homopolymerizing or randomly interpolymerizing isobutylene, 1-butene and/or 2-butene. The polybutene can be a homopolymer of any of the isomers or it can be a copolymer or a terpolymer of any of the monomers in any ratio. In an embodiment, the polybutene contains at least about 90% (wt) of isobutylene or 1-butene. In a particular embodiment, the polybutene contains at least about 90% (wt) of isobutylene. The polybutene may contain non-interfering amounts of other ingredients or additives, for instance it can contain up to 1000 ppm of an antioxidant (e.g., 2,6-di-tert-butyl-methylphenol). By way of example, the polybutene can have a molecular weight between about 150 kilodaltons and about 1,000 kilodaltons. In an embodiment, the polybutene can have between about 200 kilodaltons and about 600 kilodaltons. In a particular embodiment, the polybutene can have between about 350 kilodaltons and about 500 kilodaltons. Polybutenes having a molecular weight greater than about 600 kilodaltons, including greater than 1,000 kilodaltons are available but are expected to be more difficult to work with.

Additional alternative second polymers include diolefin-derived, non-aromatic polymers and copolymers, including those in which the diolefin monomer used to prepare the polymer or copolymer is selected from butadiene ($CH_2$=CH—CH=$CH_2$) and/or isoprene ($CH_2$=CH—C($CH_3$)=$CH_2$). In an embodiment, the polymer is a homopolymer derived from diolefin monomers or is a copolymer of diolefin monomer with non-aromatic mono-olefin monomer, and optionally, the homopolymer or copolymer can be partially hydrogenated. Such polymers can be selected from the group consisting of polybutadienes prepared by the polymerization of cis-, trans- and/or 1,2-monomer units, or from a mixture of all three monomers, and polyisoprenes prepared by the polymerization of cis-1,4- and/or trans-1,4- monomer units. Alternatively, the polymer is a copolymer, including graft copolymers, and random copolymers based on a non-aromatic mono-olefin monomer such as acrylonitrile, and an alkyl(meth)acrylate and/or isobutylene. In an embodiment, when the mono-olefin monomer is acrylonitrile, the interpolymerized acrylonitrile is present at up to about 50% by weight; and when the mono-olefin monomer is isobutylene, the diolefin is isoprene (e.g., to form what is commercially known as a "butyl rubber"). Exemplary polymers and copolymers have a molecular weight between about 150 kilodaltons and about 1,000 kilodaltons. In an embodiment, polymers and copolymers have a molecular weight between about 200 kilodaltons and about 600 kilodaltons.

Additional alternative second polymers include aromatic group-containing copolymers, including random copolymers, block copolymers and graft copolymers. In an embodiment, the aromatic group is incorporated into the copolymer via the polymerization of styrene. In a particular embodiment, the random copolymer is a copolymer derived from copolymerization of styrene monomer and one or more monomers selected from butadiene, isoprene, acrylonitrile, a $C_1$-$C_4$ alkyl(meth)acrylate (e.g., methyl methacrylate) and/or butene. Useful block copolymers include copolymer containing (a) blocks of polystyrene, (b) blocks of a polyolefin selected from polybutadiene, polyisoprene and/or polybutene (e.g., isobutylene), and (c) optionally a third monomer (e.g., ethylene) copolymerized in the polyolefin block. The aromatic group-containing copolymers contain about 10% to about 50% (wt.) of polymerized aromatic monomer and the molecular weight of the copolymer is from about 300 kilodaltons to about 500 kilodaltons. In an embodiment, the molecular weight of the copolymer is from about 100 kilodaltons to about 300 kilodaltons.

Additional alternative second polymers include epichlorohydrin homopolymers and poly(epichlorohydrin-co-alkylene oxide) copolymers. In an embodiment, in the case of the copolymer, the copolymerized alkylene oxide is ethylene oxide. By way of example, epichlorohydrin content of the epichlorohydrin-containing polymer is from about 30% to 100% (wt). In an embodiment, epichlorohydrin content is from about 50% to 100% (wt). In an embodiment, the epichlorohydrin-containing polymers have a molecular weight from about 100 kilodaltons to about 300 kilodaltons.

Non-degradable polymers can also include those described in U.S. Publ. Pat. App. No. 2007/0026037, entitled "DEVICES, ARTICLES, COATINGS, AND METHODS FOR CONTROLLED ACTIVE AGENT RELEASE OR HEMOCOMPATIBILITY", the contents of which are herein incorporated by reference in its entirety. As a specific example, non-degradable polymers can include random copolymers of butyl methacrylate-co-acrylamido-methylpropane sulfonate (BMA-AMPS). In some embodiments, the random copolymer can include AMPS in an amount equal to about 0.5 mol. % to about 40 mol. %.

Substrates

In accordance with some embodiments herein, a matrix including particles with nucleic acid complexes can be disposed on a substrate. Exemplary substrates can include metals, polymers, ceramics, and natural materials. Substrate polymers include those formed of synthetic polymers, including oligomers, homopolymers, and copolymers resulting from either addition or condensation polymerizations. Examples include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, styrene, vinyl chloride, vinyl acetate, vinyl pyrrolidone, and vinylidene difluoride, condensation polymers including, but not limited to, polyamides such as polycaprolactam, polylauryl lactam, polyhexamethylene adipamide, and polyhexamethylene dodecanediamide, and also polyurethanes, polycarbonates, polysulfones, poly(ethylene terephthalate), polytetrafluoroethylene, polyethylene, polypropylene, polylactic acid, polyglycolic acid, polysiloxanes (silicones), cellulose, and polyetheretherketone.

Embodiments of the invention can also include the use of ceramics as a substrate. Ceramics include, but are not limited to, silicon nitride, silicon carbide, zirconia, and alumina, as well as glass, silica, and sapphire.

Substrate metals can include, but are not limited to, cobalt, chromium, nickel, titanium, tantalum, iridium, tungsten and alloys such as stainless steel, nitinol or cobalt chromium. Suitable metals can also include the noble metals such as gold, silver, copper, platinum, and alloys including the same.

Certain natural materials can also be used in some embodiments including human tissue, when used as a component of a device, such as bone, cartilage, skin and enamel; and other organic materials such as wood, cellulose, compressed carbon, rubber, silk, wool, and cotton. Substrates can also include carbon fiber. Substrates can also include resins, polysaccharides, silicon, or silica-based materials, glass, films, gels, and membranes.

Medical Devices

Embodiments of the invention can include and can be used with (such as disposed on the surface of) implantable, or transitorily implantable, devices including, but not limited to, vascular devices such as grafts (e.g., abdominal aortic aneurysm grafts, etc.), stents (e.g., self-expanding stents typically made from nitinol, balloon-expanded stents typically prepared from stainless steel, degradable coronary stents, etc.), catheters (including arterial, intravenous, blood pressure, stent graft, etc.), valves (e.g., polymeric or carbon mechanical valves, tissue valves, valve designs including percutaneous, sewing cuff, and the like), embolic protection filters (including distal protection devices), vena cava filters, aneurysm exclusion devices, artificial hearts, cardiac jackets, and heart assist devices (including left ventricle assist devices), implantable defibrillators, electro-stimulation devices and leads (including pacemakers, lead adapters and lead connectors), implanted medical device power supplies (e.g., batteries, etc.), peripheral cardiovascular devices, atrial septal defect closures, left atrial appendage filters, valve annuloplasty devices (e.g., annuloplasty rings), mitral valve repair devices, vascular intervention devices, ventricular assist pumps, and vascular access devices (including parenteral feeding catheters, vascular access ports, central venous access catheters); surgical devices such as sutures of all types, staples, anastomosis devices (including anastomotic closures), suture anchors, hemostatic barriers, screws, plates, clips, vascular implants, tissue scaffolds, cerebro-spinal fluid shunts, shunts for hydrocephalus, drainage tubes, catheters including thoracic cavity suction drainage catheters, abscess drainage catheters, biliary drainage products, and implantable pumps; orthopedic devices such as joint implants, acetabular cups, patellar buttons, bone repair/augmentation devices, spinal devices (e.g., vertebral disks and the like), bone pins, cartilage repair devices, and artificial tendons; dental devices such as dental implants and dental fracture repair devices; drug delivery devices such as drug delivery pumps, implanted drug infusion tubes, drug infusion catheters, and intravitreal drug delivery devices; ophthalmic devices including orbital implants, glaucoma drain shunts and intraocular lenses; urological devices such as penile devices (e.g., impotence implants), sphincter, urethral, prostate, and bladder devices (e.g., incontinence devices, benign prostate hyperplasia management devices, prostate cancer implants, etc.), urinary catheters including indwelling ("Foley") and non-indwelling urinary catheters, and renal devices; synthetic prostheses such as breast prostheses and artificial organs (e.g., pancreas, liver, lungs, heart, etc.); respiratory devices including lung catheters; neurological devices such as neurostimulators, neurological catheters, neurovascular balloon catheters, neuro-aneurysm treatment coils, and neuropatches; ear nose and throat devices such as nasal buttons, nasal and airway splints, nasal tampons, ear wicks, ear drainage tubes, tympanostomy vent tubes, otological strips, laryngectomy tubes, esophageal tubes, esophageal stents, laryngeal stents, salivary bypass tubes, and tracheostomy tubes; biosensor devices including glucose sensors, cardiac sensors, intra-arterial blood gas sensors; oncological implants; and pain management implants.

In some aspects, embodiments of the invention can include and be utilized in conjunction with ophthalmic devices. Suitable ophthalmic devices in accordance with these aspects can provide bioactive agent to any desired area of the eye. In some aspects, the devices can be utilized to deliver bioactive agent to an anterior segment of the eye (in front of the lens), and/or a posterior segment of the eye (behind the lens). Suitable ophthalmic devices can also be utilized to provide bioactive agent to tissues in proximity to the eye, when desired.

In some aspects, embodiments of the invention can be utilized in conjunction with ophthalmic devices configured for placement at an external or internal site of the eye. Suitable external devices can be configured for topical administration of bioactive agent. Such external devices can reside on an external surface of the eye, such as the cornea (for example, contact lenses) or bulbar conjunctiva. In some embodiments, suitable external devices can reside in proximity to an external surface of the eye.

Devices configured for placement at an internal site of the eye can reside within any desired area of the eye. In some aspects, the ophthalmic devices can be configured for placement at an intraocular site, such as the vitreous. Illustrative intraocular devices include, but are not limited to, those described in U.S. Pat. No. 6,719,750 B2 ("Devices for Intraocular Drug Delivery," Varner et al.) and U.S. Pat. No. 5,466,233 ("Tack for Intraocular Drug Delivery and Method for Inserting and Removing Same," Weiner et al.); U.S. Publication Nos. 2005/0019371 A1 ("Controlled Release Bioactive Agent Delivery Device," Anderson et al.), 2004/0133155 A1 ("Devices for Intraocular Drug Delivery," Varner et al.), 2005/0059956 A1 ("Devices for Intraocular Drug Delivery," Varner et al.), and 2003/0014036 A1 ("Reservoir Device for Intraocular Drug Delivery," Varner et al.); and U.S. application Ser. Nos. 11/204,195 (filed Aug. 15, 2005, Anderson et al.), U.S. Ser. No. 11/204,271 (filed Aug. 15, 2005, Anderson et al.), U.S. Ser. No. 11/203,981 (filed Aug. 15, 2005, Anderson et al.), U.S. Ser. No. 11/203,879 (filed Aug. 15, 2005, Anderson et al.), U.S. Ser. No. 11/203,931 (filed Aug. 15, 2005, Anderson et al.); and related applications.

In some aspects, the ophthalmic devices can be configured for placement at a subretinal area within the eye. Illustrative ophthalmic devices for subretinal application include, but are not limited to, those described in U.S. Patent Publication No. 2005/0143363 ("Method for Subretinal Administration of Therapeutics Including Steroids; Method for Localizing Pharmacodynamic Action at the Choroid and the Retina; and Related Methods for Treatment and/or Prevention of Retinal Diseases," de Juan et al.); U.S. application Ser. No. 11/175,850 ("Methods and Devices for the Treatment of Ocular Conditions," de Juan et al.); and related applications.

Suitable ophthalmic devices can be configured for placement within any desired tissues of the eye. For example, ophthalmic devices can be configured for placement at a subconjunctival area of the eye, such as devices positioned extrasclerally but under the conjunctiva, such as glaucoma drainage devices and the like.

It will be appreciated that embodiments of the invention can also be used without substrates. By way of example, embodiments can include a matrix with nucleic acid complexes disposed therein in the form of a filament or other shape without including a substrate.

The present invention may be better understood with reference to the following examples. These examples are intended to be representative of specific embodiments of the invention, and are not intended as limiting the scope of the invention.

EXAMPLES

Example 1

In Situ Formation of Particles with Nucleic Acid Complexes

Polyethyleneimine (PEI) (branched 25 kDa, Sigma, St. Louis, Mo.) was dissolved in distilled deionized water (DDW) at 9 mg in 20 ml to obtain a solution having a concentration of amine groups of 10 mM. Using hydrochloric acid (HCl) the solution was adjusted to pH 7.4. 10 ul of fluorescein isothiocyanate (FITC) (Sigma, St. Louis, Mo.) 20 mg/ml was added to the solution. The progress of the reaction was followed by thin layer chromatography (TLC).

Using an N/P (nitrogen/phosphate) ratio of 6, DNA (25 ul, 1 ug/ul) ((herring sperm DNA, cleaved to 500-1000 bp, Lofstrand Labs Limited, Gaithersburg, Md.) was mixed with 6 ul 0.75 M NaCl or 6 ul of a sucrose solution in DDW (0.75 M). Fluorescein labeled-PEI as prepared above (10 mM amine conc., branched 25 kDa, 45 ul) was mixed with either 11.25 ul of 0.75 M NaCl or 11.25 ul of 0.75 M sucrose in DDW. Ending NaCl or sucrose concentration was 150 mM. The PEI solution was then slowly added to the DNA solution and then pipetted up and down 6 times, without vortexing to form a nucleic acid complex solution.

Methacrylated polyalditol (PA) (SurModics, Inc., Eden Prairie, Minn.) (100 mg/ml in 150 mM NaCl or 150 mM sucrose, 8 mg or 24 mg total) (degree of acrylate substitution of 0.5 or 12) was added to the nucleic acid complex solution. Phase separation was accomplished by addition of 1 ml of 30% w/v PEG 20 kDa solution containing 0.5 mg/ml 4,5-bis (4-benzoylphenylmethyleneoxy)benzene-1,3-disulfonic acid disodium salt. The mixture was immediately irradiated with ultraviolet light (DYMAX BLUE-WAVE 200 operating at 330 nm between about 1 and 2 mW/cm$^2$)) for 15 seconds or 1 minute. The various conditions tested are summarized in Table 1 below.

TABLE 1

| Test Condition | N = ( ) | Time of UV Irradiation | NaCL/ Sucrose | Degree of Substitution of PA |
| --- | --- | --- | --- | --- |
| 1 | 1 | 15 | NaCl | 0.5 |
| 2 | 3 | 15 | NaCl | 12 |
| 3 | 1 | 60 | NaCl | 12 |
| 4 | 3 | 60 | NaCl | 0.5 |
| 5 | 1 | 15 | Sucrose | 12 |
| 6 | 3 | 15 | Sucrose | 0.5 |
| 7 | 1 | 60 | Sucrose | 0.5 |
| 8 | 3 | 60 | Sucrose | 12 |

Figure 5A:
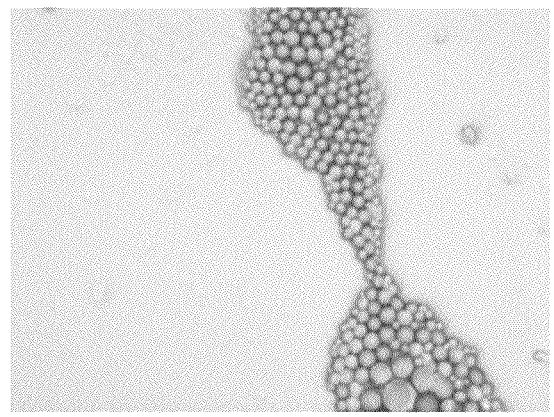
FIGS. 5A-5B are images of particles taken using fluorescence microscopy.
Figure 5B:
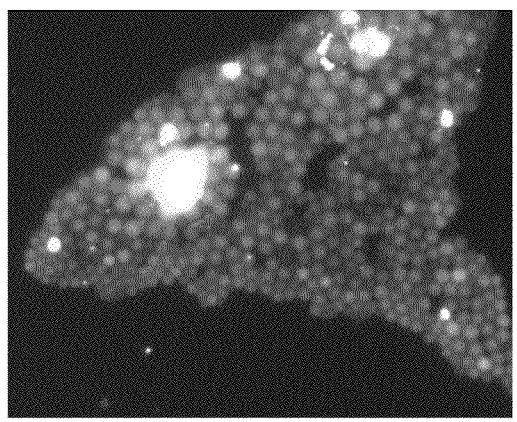

Fluorescence PEI was used to determine the encapsulation. FIGS. 5A-5B illustrate fluorescence of the particles.

Figure 6:
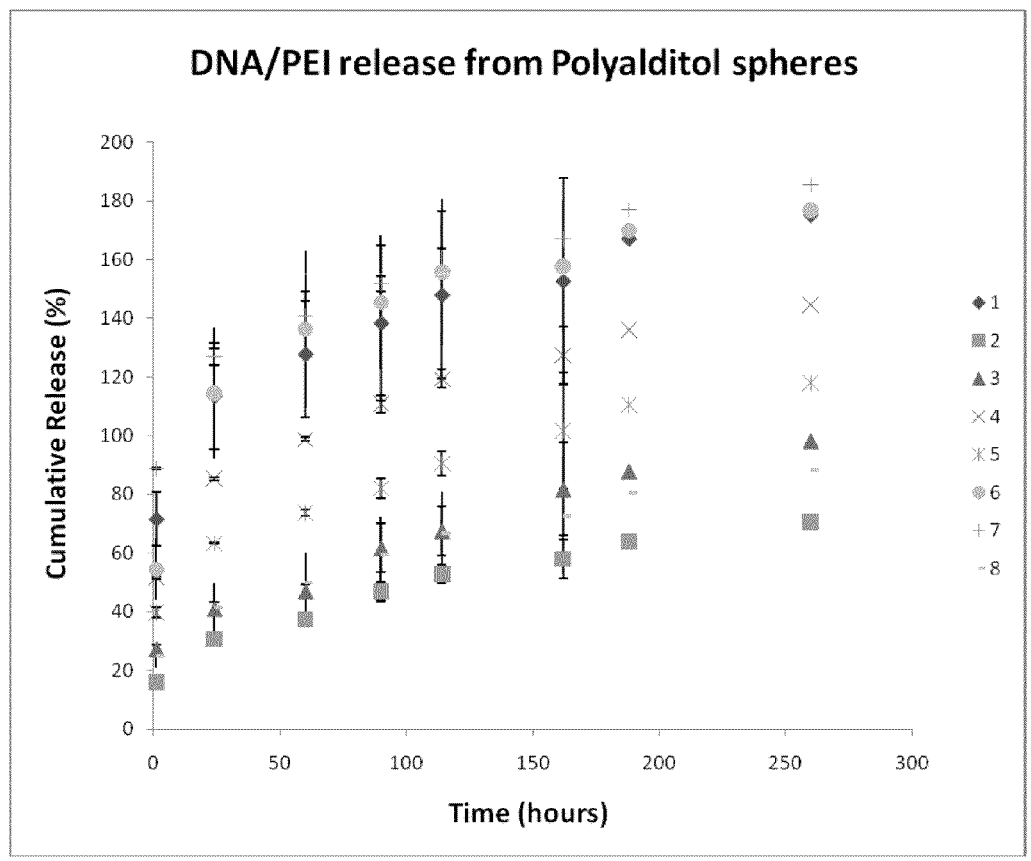
FIG. 6 is a graph showing release of nucleic acid complexes from a polyalditol particle.
Figures 9A, 9B, 9C, 9D, 9E, 9F, 9G, 9H, 9I, 9J:
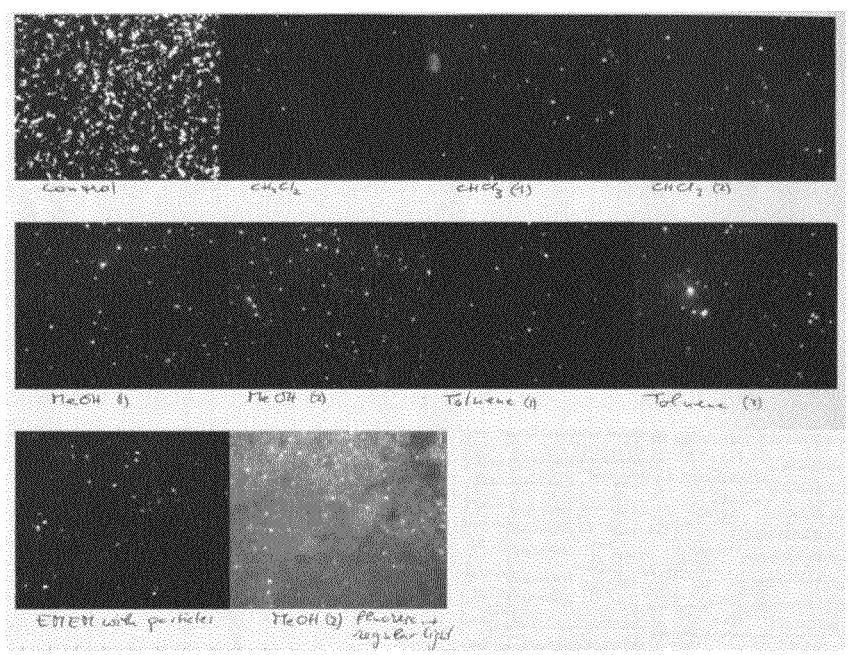
FIGS. 9A-9J are images of HEK293 cells taken using fluorescence microscopy.
Figure 10A:
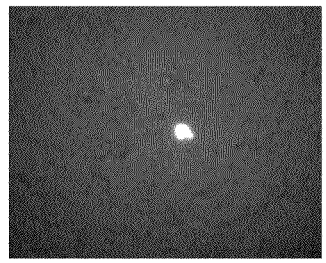
FIGS. 10A-10E are images of HEK293 cells taken using fluorescence microscopy.
Figure 10B:
Figure 10C:
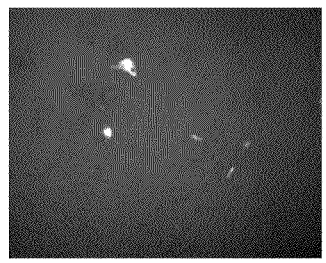
Figure 10D:
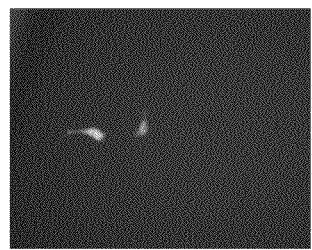
Figure 10E:

The particles were weighed and put for release in PBS. After each defined time period the PBS was exchanged and the amount of nucleic acid complexes released into the PBS was assessed by measuring fluorescence. FIG. 6 is a graph showing cumulative release of the nucleic acid complexes over time.

The results show that nucleic acid complexes can be incorporated within particles formed in situ and then can be released from the particles when put in PBS solution. With respect to burst release (or initial release of nucleic acid complexes) there was a significant effect of the loading ratio (PA/DNA ratio) and the degree of substitution of the PA. However, UV irradiation time did not affect burst release. With respect to the release profile (or linearity of release) the degree of substitution of the PA had a significant effect. UV irradiation time and NaCl vs. sucrose had minor effects on the linearity of release, while loading ratio had no effect. Regarding particle formation, no particles were formed with a low degree of substitution and a short UV irradiation period. Regarding total release, there was a strong effect of the degree of substitution of the polyalditol. However, UV irradiation had no effect on total release.

Example 2

In Situ Formation of Particles with BSA, Maltodextrin or Dextran and Transfection HEK 293 cells (ATCC, Manasass, Va.) were plated in 24-well plates at ~8×10⁴ cells/well. The cells were incubated with EMEM/10% FBS for 24 hours prior to transfection.

Maltodextrin (MD070), Dextran 35-45 kDa and BSA (bovine serum albumin) were each dissolved separately at 100 mg/ml in 0.15 M sucrose.

Nucleic acid complexes were formed with GFP-DNA (green fluorescent protein) (Aldevron, Fargo, N. Dak.) and PEI at an N/P ratio of 24. DNA (20 ul, 20 ug) was mixed with 0.75M sucrose (20 ul) and distilled deionized water (DDW) (60 ul). PEI 25 kDa was dissolved in DDW at 9 mg in total of 20 ml to obtain a solution with a concentration of 10 mM of amine groups. Using HCl the solution was neutralized to a pH 7.4. A sucrose solution 0.75 M (40 ul) and DDW (16 ul) was added to 144 ul of the PEI. The final sucrose concentration in both solutions was 0.15 M. PEI was added dropwise to the DNA; total volume was 300 ul.

600 ul of BSA, maltodextrin or dextran solution was added to 90 ul of the nucleic acid complex solution and mixed briefly. Then 700 ul of a PEG solution (PEG 20 kDa 30% w/v in DDW) was added to induce phase separation. The resulting mixture was vortexed, put on dry ice, and lyophilized. After lyophilization the PEG was extracted by adding 1 ml of chloroform and spinning the particles down at 7000 rpm for 3 minutes. The chloroform washings were performed three times and then the particles were dried.

To the samples, 1 ml of EMEM was added. 0.5 ml of the EMEM/particle mixture was then put on cells in the 24-well plate. After 48 hours GFP expression was observed using a fluorescent microscope. It was observed that the best expression was achieved when using dextran. BSA was found to reduce the transfection efficiency more than maltodextrin. This example shows that particles containing nucleic acid complexes can be formed in situ using BSA, dextran, and maltodextrin and that the nucleic acid complexes therein can retain their activity in order to transfect cells.

Example 3

Nucleation with Nucleic Acid Complexes

Polyethyleneimine (PEI, Sigma, 25 kDa branched) was dissolved at 9 mg in 10 mL distilled deionized water (DDW). Using HCl the initial basic pH was brought back to 7.4 and total volume was adjusted with DDW to 20 mL (creating 10 mM primary amino groups or "N"). Herring DNA 600-1000 bp (Lofstrand, Gaithersburg, Md.) was dissolved in DDW at 1 µg/µL. 1 µg DNA contains 3 nmol of negatively charged phosphate groups ("P"). DNA was mixed with PEI to provide DNA/PEI solutions with N/P ratios of 12 and 24, individually.

For a N/P ratio of 12, 5.5 µg DNA (5.5 µL) was mixed with 13.8 µL sucrose 0.75 M (2.57 g in 10 ml water, 25% w/v) to yield a 150 mM or 5% w/v solution. 20 µL of the PEI solution was mixed with 4 µL of the 0.75 M sucrose solution. The PEI mixture was dropped slowly into the DNA solution. After addition the mixture was vortexed briefly.

For a N/P ratio 24:2.75 µg DNA (2.75 µL) was mixed with 0.7 µL sucrose 0.75 M (2.57 g in 10 ml water, 25% w/v) to yield a 150 mM or 5% w/v solution. The PEI solution in an amount of 20 tL was mixed with 4 µL 0.75 M sucrose solution. The PEI mixture was dropped slowly into the DNA solution. After addition the mixture was vortexed briefly.

200 µl of protein (Fab) (Southern Biotech) at 20 mg/ml at pH 7.4 was added to the DNA/PEI nucleic acid complex solutions individually at room temperature and the samples were put in an oven at 50° C. for 20 minutes. After this, 70 µL of a PEG 20 kDa solution 30% w/v (warmed to 50° C.) was added dropwise to the nucleic acid complex/protein mixture while vortexing several seconds.

The samples were either put back immediately in the oven for 30 minutes at 50° C. or left out the oven and put at room temperature for 30 minutes. Subsequently the mixtures were put in the freezer at −20° C. until frozen and lyophilized. The PEG was extracted with chloroform. This example shows that particles can be formed with nucleic acid complexes and protein wherein the nucleic acid complexes serve as a nucleation agent.

Example 4

Formation of Coil with Coating Including Particles with Nucleic Acid Complexes and Transfection A DNA solution was prepared by mixing 200 ug DNA (40 ul, green fluorescent protein (GFP) encoding plasmid) with 10 ul sucrose 0.75 M in DDW.

A PEI solution was prepared by mixing 1.44 ml polyethylenimine (0.45 mg/ml in DDW, pH 7.4 as adjusted with several drops of 0.1N HCl; 10 mM amine-groups) with 360 ul sucrose 0.75 M in DDW. The PEI solution was sterilized by filtration through a 0.2 µm filter.

A dextran solution was prepared by mixing 100 mg/ml dextran in 0.150 M sucrose (in DDW). The dextran solution was sterilized by filtration through a 0.2 µm filter.

A PEG solution was prepared by mixing 30% w/v PEG 20 kDa in DDW. The PEG solution was sterilized by filtration through a 0.2 µm filter.

The PEI solution was added to the DNA solution slowly, pipetted up and down 6 times and left for 5 minutes at room temperature forming a nucleic acid complex mixture. 500 ul dextran solution (100 mg/ml in 0.150M sucrose) was added forming a dextran/nucleic acid complex mixture.

As a control, 5 ul of the resulting mixture was put in a 24-well, seeded with HEK293 cells (90% confluent).

To the dextran/nucleic acid complex mixture 7 ml of the PEG solution was added. The resulting suspension was vortexed briefly, put on dry ice and lyophilized.

The PEG was extracted as follows: 40 ml of chloroform was added and the suspension was divided over 4 15-ml centrifuge tubes. After spinning for 10 mins at 7.5 krpm the chloroform was aspirated and discarded. A sample was dried, dissolved in EMEM and put on cells in 24-well plate. After 48 hours transfection was seen as shown in FIG. 7.

The residues were combined in fresh chloroform and put in Millipore centrifugal filtration tubes (Ultrafree-CL, 0.2 µm Teflon filter). The dextran particles were washed 3 times with chloroform and filtered each time at 7.5 krpm.

The solids were then collected in 15 ml chloroform and homogenized (Silverson, 8000 rpm). The resulting suspension was filtered (Buchner, 20 µm filter). 25 mg 1000PEG45PBT55 (block copolymer of 45 wt. % 1000 mw polyethylene glycol "PEG" and 55 wt. % polybutylene terephthalate "PBT") and 25 mg 20GAPEGCL80GALA (block copolymer of 20 wt. % glycolide-polyethylene glycol-caprolactone "GAPEGCL" and 80 wt. % glycolide-lactide "GALA") were added to 50 mg of dextran/polyplex particles in chloroform, which dissolved while shaking at 37 degrees C./for 30 minutes. The resulting mixture was then used to coat metal eye implants (N=8) (I-VATION™, SurModics, Eden Prairie, Minn.). The implants were coated (coating weight 1700-2000 mg) using gas atomization type spray coater in two series of 4 implants and then dried under nitrogen over night. The coating weights for the implants are shown below in Table 2.

TABLE 2

| COATING WEIGHTS | SERIES 1 | SERIES 2 |
|---|---|---|
| 1 | 1872 | 1666 |
| 2 | 2063 | 1872 |
| 3 | 2137 | 1849 |
| 4 | 2007 | 1736 |

HEK 293 cells were plated in a 96-well plate. The cells were incubated with EMEM/10% FBS for 24 hours prior to transfection experiment. The cells were found to be confluent prior to the elution experiment. The implants were briefly dipped in isopropyl alcohol, dipped dry and each put in an individual well on top of the HEK 293 cells. After 24 hours, transfection was assessed using fluorescence microscopy and the implants were moved to different wells. Fluorescence for coil #2 (first series) is shown below in FIG. 8A. Fluorescence for coil #3 (first series) is shown below in FIG. 8A.

Example 5

Incorporation of Nucleic Acid Complexes Into Preformed Particles

For this example, nucleic acid complexes were incorporated into various particles. nucleic acid complex solution (GFP encoding DNA with PEI, N/P=24) was prepared and was pipetted onto specific amount of powder, mixed well, and dried in vacuum. Then the powder was re-suspended in cell medium (EMEM). Part was spun down and supernatant was put on HEK 293 cells, part was put on cells as a suspension.

The porous particulate materials included a ground porous ceramic. A ceramic disk with 0.5 µm pores was obtained and then ground with a mortar and pestel to particles with an average size less than 10 µm in size (as verified by SEM).

The porous particulate materials also included kaolin particles. The kaolin particles had an average size less than 5 µm.

The porous particulate materials also included cross linked polyvinylpyrollidone (cross-PVP) particles (BASF Corporation). The cross-PVP particles had an average size of less than 10 µm.

The porous particulate materials also included cross linked methacrylate maltodextrin particles. The cross linked methacrylate maltodextrin particles were formed by the following process. First, a 100 mg/ml methacrylated maltodextrin M40 mixture was phase separated by adding 30% w/v PEG 20 kDa solution containing 5 mg/ml 4,5-bis(4-benzoylphenylmethyleneoxy)benzene-1,3-disulfonic acid disodium salt. The mixture was UV irradiated (DYMAX BLUE-WAVE 200 operating at 330 nm between about 1 and 2 mW/cm$^2$) for 1 minute. The crosslinked particles were spun and then the PEG was decanted. The crosslinked particles were then washed with DDW.

Nucleic acid complexes were prepared at N/P ratio 24. Typically, 12 ul of DNA solution 1 ug/ul (12 ug) was mixed with 12 ul of a 0.75 M sucrose solution and 36 ul of DDW. 86.4 ul of a PEI solution (10 mM [N]) was mixed with 24 ul of a 0.75 M sucrose solution and 9.6 ul of DDW. The resulting PEI mixture was added to the DNA solution to form a nucleic acid complex solution and left for 5 minutes. The nucleic acid complex solution was divided into portions of 15 ul (1 ug of DNA each).

One 15 ul sample was taken as control and put on cells in 24-well plate. The other 15 ul samples of the nucleic acid complex solution were put on 2 or 10 mg of solid material (ceramic, kaolin, cross-PVP, or cross linked methacrylate maltodextrin). After incubation for 10 minutes at room temp, a sample was taken from each well and added to EMEM and then put over HEK293 cells in a 24-well plate. The remainder (particles) of each sample was dried in a vacuum oven for 1 hour. EMEM was added to the dried particles and vortexed well. Then the mixture was spun at 5 krpm for 5 minutes. The supernatant was put on HEK293 cells in a 24 well-plate. The residue (pellet) was resuspended in EMEM and added to a 24-well plate over HEK293 cells as well, forming a "blanket". The cells could no longer been seen under a light microscope. The transfection results are shown below in Table 3.

TABLE 3

| Particle Type | 2 mg, supernatant | 2 mg, direct on cells | 10 mg, supernatant | 10 mg, direct on cells |
|---|---|---|---|---|
| PVP-CM (BASF) | Transfection | Lot of Transfection | No Transfection | Lot of Transfection |
| Ceramic | No Transfection | Some Transfection | No Transfection | No Transfection |
| Kaolin | No Transfection | Little Transfection | No Transfection | No Transfection |
| MD-particles | More Transfection | Little Transfection | Little Transfection | More Transfection |

Example 6

Cross-PVP Particles in Organic Solvents

HEK293 cells were plated in 24-well plate 48 hours in advance. DNA/PEI nucleic acid complexes were prepared in 5% sucrose at N/P ratio 15 (7 ug DNA, 140 ul total volume). 10 ul aliquots of a DNA solution (0.5 ug) were put in two separate wells as a control. The remaining 120 ul was pipetted into six microcentrifuge tubes (20 ul each) containing 5 mg cross-PVP particles. The tubes were vortexed well, opened, and left to dry in vacuum at RT for two hours The following solvents were added to tubes 1-5 (0.5 ml): DCM, Chloroform, MeOH, THF and Toluene and vortexed well. Tube 6 served as a control. After spinning (10 krpm, 5 minutes) the solvents were aspirated from tubes 1-5. The remaining solvent was removed under vacuum. EMEM (cell medium, 200 ul) was added to each the tubes. The particles were suspended by using a 200-ul pipette and the suspension was divided over two wells of HEK293 cells.

After resuspending the particles of tube 6 in EMEM, the suspension was spun down. The supernatant was divided over two wells. Again, EMEM was added and the particles were resuspended. The suspension was then also divided over two wells of HEK293 cells.

After incubation for 48 hours transfection was assessed using fluorescence microscopy. Images are shown in FIGS. 9A-9J.

From qualitative measurements using the fluorescent microscope, it can be seen that most solvents can be used but the best results were obtained after treatment with methanol. The PVP particles form a blanket over the plated cells, which accounts for a large part for the attenuation in fluorescent signal. After treating the particles with THF, no transfection was seen at all. Similarly, when incubating cells with EMEM, after 5 minutes incubation at room temperature and spinning the particles down, no transfection was seen. This indicates that the PVP particles do not immediately release the nucleic acid complexes.

Example 7

Cross-PVP Particles with Elution in Aqueous Solvent and Transfection

For this study, 10 μm-diameter cross-PVP particles (PVP-CM, BASF) were used. Nucleic acid complexes N/P=24 were prepared by adding 360 ul of a PEI solution, 100 ul of a 0.75 M sucrose solution and 40 ul DDW with 50 ul of a 1 ug/ul GFP-DNA solution, 50 ul of a 0.75M sucrose solution, and 150 ul DDW. The resulting nucleic acid complex solution was left at RT for 5 minutes and then added to cross-PVP particles 100 mg. The mixture was vortexed well, allowed to absorb, and dried under vacuum.

The dried powder was re-suspended in a solution of chloroform and added polymers (1000PEG45PBT55 and 20GAPEGCL80GALA). The resulting solution included particles 50% w/w, 1000PEG45PBT55 25 mg (25% w/w) and 20GAPEGCL80GALA 25 mg (25% w/w). Due to swelling of the cross-povidone, the suspension was not filtered. Next, the solution was sprayed onto coils with a gas atomization type spray system. This air-pressure based spray system coated the coils one at the time. The coils were dried under nitrogen and then put onto HEK293 cells in 96-well-plates. Weights of the coils are shown below in Table 4.

TABLE 4

| Coil # | Coating weight (mg) |
|---|---|
| 1 | 1.703 |
| 2 | 1.085 |
| 3 | 1.786 |
| 4 | 0.321 |

After three days, the coils were transferred to other wells and this was repeated after six and nine days. After three days some transfection was seen. After additional three days only one or two cells were transfected. No further effects on cells were seen after six days. Fluorescence microscopy images of the cells are shown in FIGS. 10A-E.

Example 8

Nucleic Acid Complexes with Varying Amounts of PVP Particles

Nucleic acid complexes (N to P ratio=24) were prepared by adding 1440 ul of a PEI solution and 205 ul of a 0.75 M sucrose solution to 200 ul of a 1 ug/ul DNA solution and 205 ul of a 0.75M sucrose solution. The resulting nucleic acid complex solution was left at RT for 30 minutes. 2 mg, 4 mg, 8 mg, and 10 mg of crosslinked PVP particles (BASF Kollidon Cl-M Lot #87825288Q0) were added to samples of 50 ul DNA polyplexes that contained 5 ug of DNA. The particles were not freeze dried, but isolated, weighed and put into 100× HEPES buffer for elution testing.

Elution samples were placed into the 37° C. oven overnight and then tested the following day using an ethidium bromide/heparin assay. The following solutions were prepared for the ethidium bromide/heparin assay: a.) heparin sodium salt (Celsus Lot #PH-39899) 15 mg/mL in distilled deionized water (DDW), and b.) ethidium bromide (EtBr) Sigma Aldrich tablets dissolved in DDW to form a 1000× solution (this solution was diluted to 100× in DDW).

For the ethidium bromide/heparin assay a stock DNA solution of 50 ug/ml was prepared. Standards were prepared at 100 uL per well in a 96 well black bottom plate (Grenier Bio-one) by serially diluting starting at 25 ug/mL DNA and diluting down to 195 ng/mL. 10 ul of 100× ethidium bromide solution was added to each sample. Samples were read using an M2 Spectromax plate reader under the following parameters: excitation 273 nm/emission 603 nm/cutoff 570 nm. DNA in polyplex form would not give any fluorescence, as opposed to naked DNA. Then 100 ul freshly prepared heparin solution added to the samples. The plate was read again at 5 minutes intervals until optimal reading was obtained (after approximately 10 minutes). The results of this assay are shown below in Table 5:

TABLE 5

| Sample | ug DNA Released (mean) | % Released |
|---|---|---|
| PVP 10 mg | 1.622 | 35.7 |
| PVP 8 mg | 2.461 | 54.2 |
| PVP 4 mg | 3.093 | 68.1 |
| PVP 2 mg | 4.397 | 96.9 |

The experiment was then repeated with the addition of a second N/P ratio (both 24 and 10) and freeze drying. Specifically, DNA polyplexes were formed as described above, however for one batch the N:P ratio was 24 while for another batch the N/P ratio was 10 (while still holding to 20% (w/v) sucrose for both). For this experiment the amounts of PVP particles used were 2 mg, 6 mg, and 10 mg. This time, particles were freeze dried overnight and then put into 100× HEPES buffer for elution testing. Elution samples were placed into the 37° C. oven and then tested at 6 hrs and after 1 day using the ethidium bromide/heparin assay described above. The results are shown below in Table 6 and in FIGS. 11A (6 hours) and 11B (24 hours).

TABLE 6

| mg PVP | N:P Ratio | 6 Hours | | 24 Hours | |
|---|---|---|---|---|---|
| | | ug DNA Released (mean) | % Released | ug DNA Released (mean) | % Released |
| 2.24 | 24 | 4.816 | 96.32 | 4.91 | 98.2 |
| 6.24 | 24 | 2.879 | 57.58 | 3.054 | 61.08 |
| 10.24 | 24 | 0.663 | 13.26 | 0.726 | 14.52 |
| 2.1 | 10 | 4.89 | 97.8 | 4.89 | 97.8 |
| 6.1 | 10 | 0.176 | 3.52 | 1.015 | 20.3 |
| 10.1 | 10 | 0 | 0 | 0 | 0 |

Different correlations between the amounts of PVP particles added to the DNA polyplex solution and the percent released after 24 hours when incubated at 37° C. were found for different N/P ratios, as determined by the ethidium bromide/heparin assay. Specifically, a linear correlation between milligrams of PVP and percent of DNA released was found when using polyplexes with an N/P ratio of 24. This correlation was preserved even after freeze-drying the mixtures.

Example 9

Addition of Proteins and Maltodextrin Derivatives to Peptide/siRNA Complexes in the Formation of Discrete Particles by Phase-Separation Proteins solutions (IgG and Fab) were prepared as follows: Fab in PBS (Southern Biotech) or IgG (lyophilized, Lampire, reconstituted in slightly acidic PBS with drop of HCl) were put on BioRad desalting column and eluted with 10 mM Ps/no NaCl. Using a centrifuge filter the protein solutions were concentrated to approximately 40 mg/ml.

SiRNA complexes (1.5 ul 20 uM siRNA per group) were formed with 3.75 ul N-ter in 50 ul N-ter specific buffer. Typically 6 to 9 times of the amounts were mixed and the resulting siRNA/Nter complexes in buffer were then divided in 50 ul portions. Similar samples were prepared both for anti-luciferase siRNA as well as non-coding (scrambled) siRNA. To the samples 50 ul of each of the following solutions was added: BSA at 40 mg/ml, IgG at 40 mg/ml in 10 mM Ps (phosphate, no NaCl), Fab at 40 mg/ml in 10 mM Ps (phosphate, no NaCl), MD-acrylate at 40 mg/ml in DDW, MD-hydrazide at 40 mg/ml in DDW.

To the solutions 400 ul PEG 20 kDa 30% w/w in DDW was added while vortexing. Where phase-separation occurred a white suspension was formed. Particles were spun down and PEG phase was discarded. To the resulting particle residues 350 ul DMEM (with FBS and 5 ug/ml doxycycline) was added and vortexed thoroughly. Control samples were prepared (with luciferase and scrambled siRNA) by adding 1.5 ul siRNA to 45 ul N-ter Buffer. To the solution 3.75 ul N-ter was added and vortexed. The sample was diluted in 300 ul DMEM/10% FBS/5 ug/ml doxycycline.

HR5CL11 doxyclin-induced luciferase expressing cells were plated at $10^4$ cells/well in clear bottom black 96-well plates and incubated 24 hours prior to transfection.

100 ul was added to 42 wells with HR5CL11 cells (siRNA at 86 nM concentration), then 450 ul DMEM was added and 100 ul was added to 43 wells (siRNA at 21 nM concentration). Again, 450 ul DMEM was added and 100 ul was added to 3 wells (siRNA at 7 nM concentration).

Figure 12:
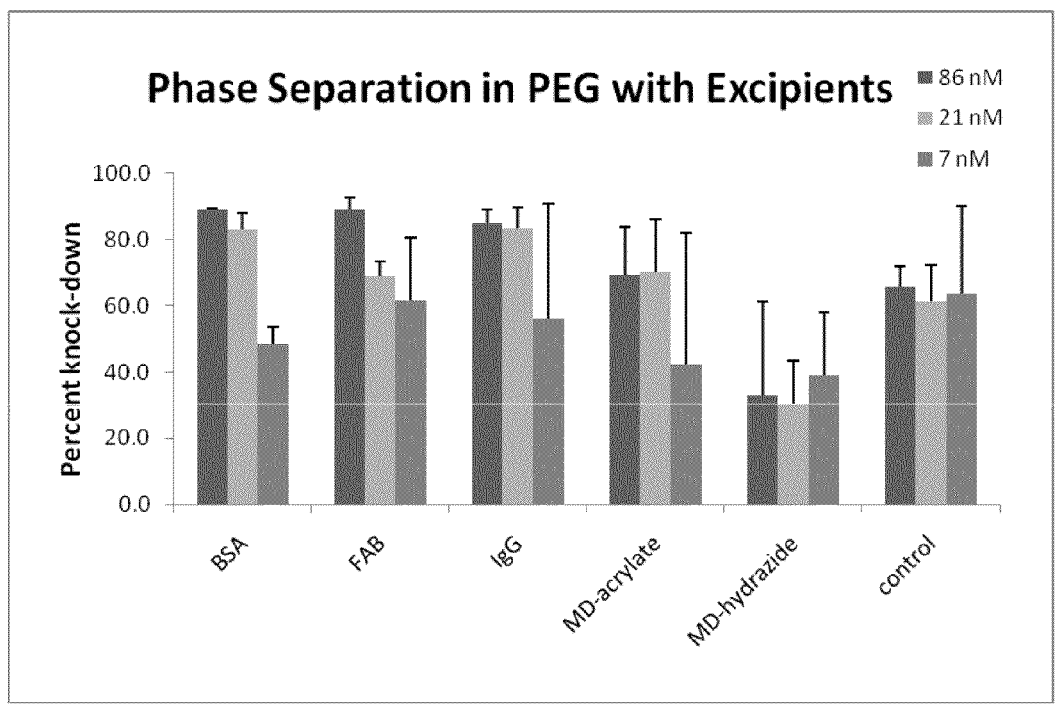
FIG. 12 is a graph showing percent knock-down of luciferase expression as a result of transfection with siRNA.

24 hours after transfection all media was removed. The cells were first incubated with Cell Titre Blue (1 part reagent with 4 parts DMEM/10% FBS; doxycycline was added to end concentration of 5 ug/ml) to conduct toxicity assessments. After incubation for 1.5 hours the plate was read using fluorescence ($\lambda_{ex}$=560 nm, $\lambda_{em}$=590 nm). The cells were then washed once with PBS and lysed using 50 ul Glo lysis buffer (Promega). Luciferin reagent was added (50 ul) and the level of luciferase expression was measured using chemiluminescence. The data are shown in FIG. 12.

Example 10

Effect of Organic Solvents on Peptide/siRNA Complexes with IgG in Particles

SiRNA complexes (1.5 ul 20 uM siRNA per group) were formed with 3.75 ul N-ter in 50 ul N-ter specific buffer. Typically 6 to 9 times of the amounts were mixed and the resulting siRNA/Nter complexes in buffer were then divided in 50 ul portions. Similar samples were prepared both for anti-luciferase siRNA as well as non-coding (scrambled, control) siRNA.

To the samples 50 ul of IgG at 40 mg/ml in 10 mM Ps (phosphate, no NaCl) was added. To the solutions 400 ul PEG 20 kDa 30% w/w in DDW was added while vortexing. Where phase-separation occurred a white suspension was formed. Particles were spun down and PEG phase was discarded.

To the resulting residue first an aliquot of IPA was added and drawn off to remove residual water. Then the following solvents were added (0.4 ml) to the particles and vortexed thoroughly: dichloromethane, chloroform, ethylacetate, cyclohexane. To one group of particles, no solvent was added. Instead, the particles were immediately redissolved in 300 ul DMEM/10% FBS/5 ug/ml doxycycline ("particles" in graph).

After vortexing, the organic phase was removed from the particles by evaporating under vacuum. To the resulting residues 600 ul DMEM (with FBS and 5 ug/ml doxycycline) was added and vortexed thoroughly. Control samples were prepared (with luciferase and scramble siRNA) by adding 1.5 ul siRNA to 45 ul N-ter buffer. To the solution, 3.75 ul N-ter was added and vortexed. The sample was diluted in 250 ul DMEM/10% FBS/5 ug/ml doxycycline.

HR5CL11 doxyclin-induced luciferase expressing cells were plated at $10^4$ cells/well in clear bottom black 96-well plates and incubated 24 hours prior to transfection.

Figure 13:
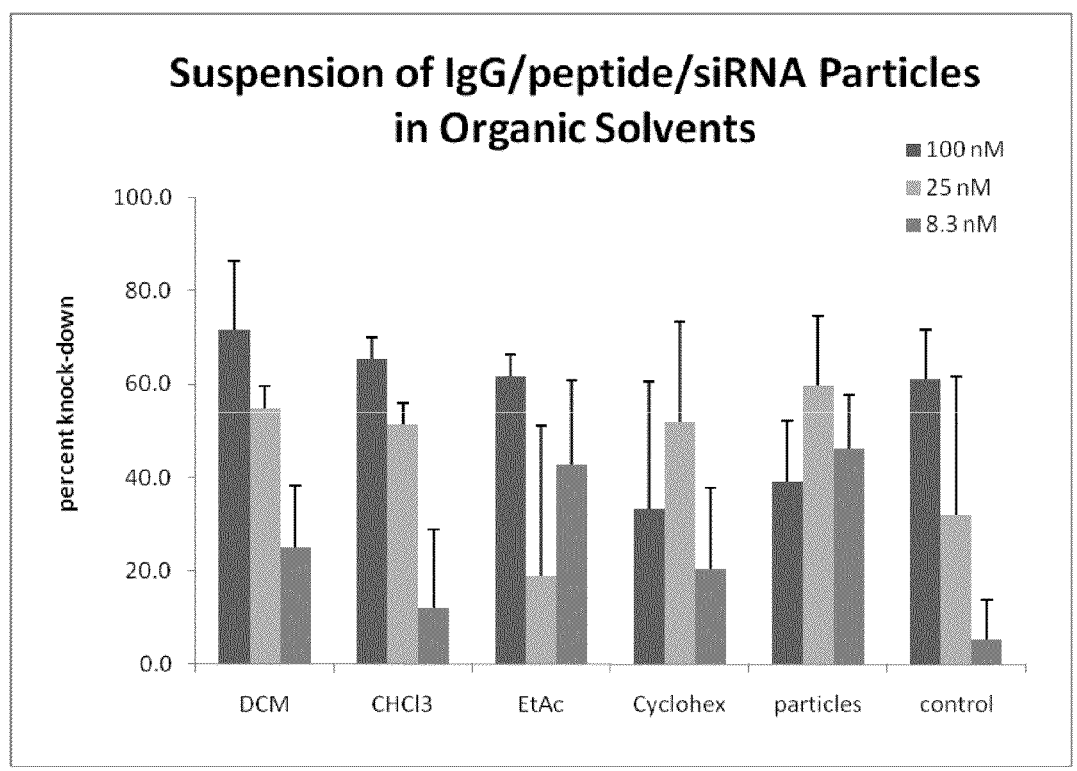
FIG. 13 is a graph showing percent knock-down of luciferase expression as a result of transfection with siRNA.

100 ul was added to 42 wells with HR5CL11 cells (siRNA at 100 nM concentration), then 300 ul DMEM was added and 100 ul was added to 3 wells (siRNA at 25 nM concentration). Again, 200 ul DMEM was added and 100 ul was added to 43 wells (siRNA at 8.3 nM concentration). Percent knock-down was calculated as described in example 9 above. The data are shown in FIG. 13.

Example 11

Effect of Organic Solvent on Peptide/siRNA Complexes with HuSA or Glycogen in Particles SiRNA complexes (1.5 ul 20 uM siRNA per group) were formed with 3.75 ul N-ter in 50 ul N-ter specific buffer. 5 times of the amounts were mixed and the resulting siRNA/Nter complexes in buffer were then divided in 50 ul portions. Similar samples were prepared both for anti-luciferase siRNA as well as non-coding (scrambled, control) siRNA. To the samples 50 ul of the following solutions was added: HuSA (human serum albumin) at 40 mg/ml, glycogen at 40 mg/ml.

To the solutions 400 ul PEG 20 kDa 30% w/w in DDW was added while vortexing. Where phase-separation occurred a white suspension was formed. Particles were spun down and the PEG phase was discarded.

To the resulting residues of one set of samples 600 ul DMEM (with FBS and 5 ug/ml doxycycline) was added and vortexed thoroughly (siRNA is here at 50 nM concentration). To the resulting residues of another set of samples first an aliquot of IPA was added and drawn off to remove residual water. To the particles dichloromethane was added (0.4 ml) and vortexed thoroughly. Subsequently solvent was removed by evaporation under vacuum. 600 ul DMEM (with FBS and 5 ug/ml doxycycline) was added to the dry particles and vortexed thoroughly (siRNA is here at 50 nM concentration).

Control samples were prepared (with luciferase and scrambled siRNA) by adding 1.5 ul siRNA to 45 ul N-ter Buffer. To the solution 3.75 ul N-ter was added and vortexed. The sample was diluted in 550 ul DMEM/10% FBS/5 ug/ml doxycycline.

HR5CL11 doxyclin-induced luciferase expressing cells were plated at $10^4$ cells/well in clear bottom black 96-well plates and incubated 24 hours prior to transfection.

Figure 14:
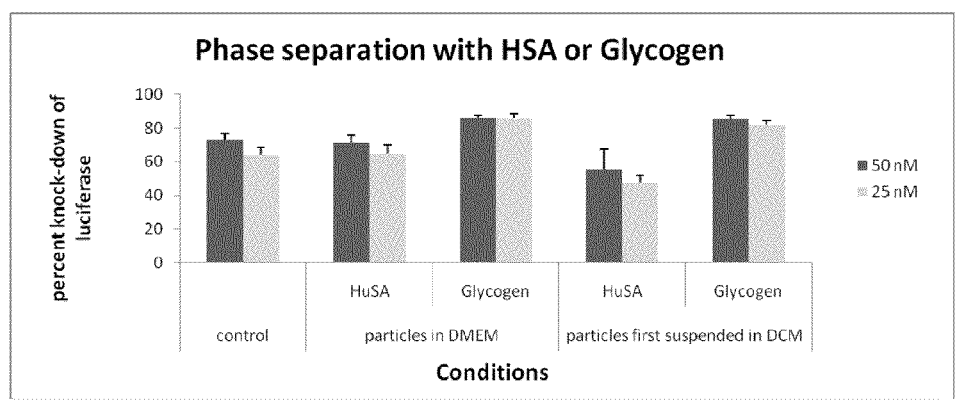
FIG. 14 is a graph showing percent knock-down of luciferase expression as a result of transfection with siRNA.
Figure 15:
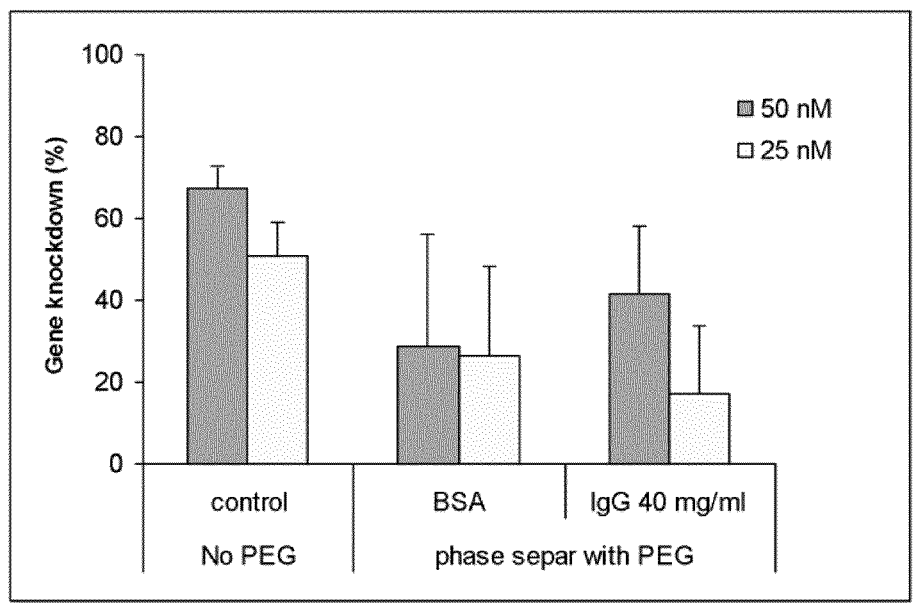
FIG. 15 is a graph showing percent knock-down of luciferase expression as a result of transfection with siRNA.

100 ul was added to 4 wells with HR5CL11 cells (siRNA at 50 nM concentration), then 200 ul DMEM was added and 100 ul was added to 4 wells (siRNA at 25 nM concentration). The data are shown in FIG. 14.

Example 12

Addition of Proteins to DOTAP/siRNA Complexes in the Formation of Discrete Particles by Phase-Separation DOTAP (Avanti Polar Lipids) and Cholesterol were dissolved in ethanol at 1 mg/ml and mixed at a DOTAP/Cholesterol ratio of 9:1. SiRNA complexes (1.5 ul 20 uM siRNA per group) were formed with 4.2 ul of the DOTAP/Cholesterol mixture in 45 ul double distilled water. Typically 6 to 9 times of the amounts were mixed and the resulting siRNA/Nter complexes in buffer were then divided in 50 ul portions. Similar samples were prepared both for anti-luciferase siRNA as well as non-coding (scrambled, control) siRNA.

An IgG protein solution (IgG) was prepared as follows: IgG (lyophilized, Lampire, reconstituted in slightly acidic PBS with drop of HCl) was put on BioRad desalting column and eluted with 10 mM Ps/no NaCl. Using a centrifuge filter the protein solution was concentrated to approximately 40 mg/ml.

To the samples 50 ul of the following solutions was added: BSA at 40 mg/ml, or IgG at 40 mg/ml in 10 mM Ps (phosphate, no NaCl).

To the solutions 400 ul PEG 20 kDa 30% w/w in DDW was added while vortexing.

Where phase-separation occurred a white suspension was formed. Particles were spun down and PEG phase was discarded.

To the resulting residues 600 ul DMEM (without FBS, but with 5 ug/ml doxycycline) was added and vortexed thoroughly (siRNA is here at 50 nM concentration).

Control samples were prepared (with luciferase and scrambled siRNA) by adding 1.5 ul siRNA to 45 ul DDW. To the solution 4.2 ul of the DOTAP/Cholesterol mixture was added and vortexed. The sample was diluted in 550 ul DMEM/10% FBS/5 ug/ml doxycycline.

HR5CL11 doxyclin-induced luciferase expressing cells were plated at $10^4$ cells/well in clear bottom black 96-well plates and incubated 24 hours prior to transfection.

100 ul was added to 4 wells with HR5CL11 cells (siRNA at 50 nM concentration), then 200 ul DMEM was added and 100 ul was added to 4 wells (siRNA at 25 nM concentration). After incubating for 3 hours at 37° C., the medium was replaced with DMEM/10% FBS/5 ug/ml doxycycline).

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference. Nothing herein is to be construed as an admission that the inventors are not entitled to antedate any publication and/or patent, including any publication and/or patent cited herein.

The invention has been described with reference to various specific and preferred embodiments and techniques. However, it should be understood that many variations and modifications may be made while remaining within the spirit and scope of the invention.

Further Embodiments:

In an embodiment the invention includes a method of forming particles with nucleic acid complexes including contacting nucleic acids with cationic carrier agents to form nucleic acid complexes and absorbing the nucleic acid complexes to porous particles, the particles having an average diameter of less than about 100 µm. In an embodiment, of the method the particles have an average diameter of equal to or less than 40 µm. In an embodiment, the particles have an average diameter of equal to or less than 10 µm. In an embodiment, the porous particles are configured to release the nucleic acid complexes in vivo. In an embodiment, the porous particles comprise a material selected from the group consisting of ceramics, kaolin, and cross-linked polymers. In an embodiment, the cationic carrier agent includes polyethyleneimine (PEI). In an embodiment, the method includes contacting nucleic acids with cationic carrier agents to form nucleic acid complexes, contacting the nucleic acid complexes with a polymer; and cross-linking the polymer. In an embodiment, the method further comprises performing phase separation after the step of contacting the nucleic acid complexes with the polymer. In some embodiments, cross-linking the polymer can comprise applying ultraviolet light to the polymer. In some embodiments, cross-linking the polymer can comprise adding a cross-linking agent.

In an embodiment, the invention includes a method of forming particles with nucleic acid complexes. The method can include contacting nucleic acids with cationic carrier agents to form nucleic acid complexes and contacting the nucleic acid complexes with a solution comprising a protein, the nucleic acid complexes acting as a nucleating agent for the protein. In an embodiment, the method can include performing phase separation after the step of contacting the nucleic acid complexes with the solution comprising a protein. In an embodiment, the protein can include Fab fragments.

In an embodiment, the invention can include a method of making a medical device including contacting nucleic acids with cationic carrier agents to form nucleic acid complexes; adsorbing the nucleic acid complexes to porous particles to form nucleic acid complex containing particles; mixing the nucleic acid complex containing particles with a polymer solution to form a coating mixture; and applying the coating mixture to a substrate. The porous particles can include a material selected from the group of ceramics, kaolin, and cross-linked polymers. The cationic carrier agent can include polyethyleneimine (PEI). The polymer solution can include a degradable polymer. The polymer solution can include a non-degradable polymer. The polymer solution can include an organic solvent. Applying the coating mixture to a substrate can include spraying the coating mixture onto the substrate.

In an embodiment, the invention can include a method of making a medical device including contacting nucleic acids with cationic carrier agents to form nucleic acid complexes; adsorbing the nucleic acid complexes to a porous material to form nucleic acid complex containing particles; mixing the nucleic acid complex containing particles with a polymer solution to form a coating mixture; and curing the coating mixture.

In an embodiment, the invention can include a method of making a medical device including contacting nucleic acids with cationic carrier agents to form nucleic acid complexes; combining the nucleic acid complexes with a material to form nucleic acid complex containing particles in situ; mixing the nucleic acid complex particles with a polymer solution to form a coating mixture; and applying the coating mixture to a substrate.

In an embodiment, the invention can include an implantable medical device including a substrate; an elution control matrix disposed on the substrate; a plurality of particles disposed within the elution control matrix; and a plurality of nucleic acid complexes disposed within the particles, the nucleic acid complexes comprising a nucleic acid and a cationic carrier agent.

In an embodiment, the invention can include an implantable medical device including an elution control matrix; a plurality of particles disposed within the elution control matrix; and a plurality of nucleic acid complexes disposed within the particles, the nucleic acid complexes comprising a nucleic acid and a cationic carrier agent.

The invention claimed is:

1. An active agent delivery device comprising:
   nucleic acid complexes comprising a nucleic acid and a cationic carrier agent;
   a polymeric excipient comprising glycogen, wherein the nucleic acid complexes and the polymeric excipient form polymeric particles in which the nucleic acid complexes are encapsulated, the polymeric particles having an average diameter of less than about 100 um, and
   an elution control matrix, wherein the polymeric particles are disposed within the elution control matrix.

2. The active agent delivery device of claim 1, wherein the particles are configured to maintain the transfection properties of the nucleic acid complexes despite exposure to organic solvents.

3. The active agent delivery device of claim 1, further comprising between 0 percent by weight and 5 percent by weight of an amphiphilic polymer.

4. The active agent delivery device of claim 3, the amphiphilic polymer comprising polyethyleneglycol.

5. The active agent delivery device of claim 1, the cationic carrier agent comprising one or more of a peptide, a lipid, or a cationic polymer.

* * * * *